US00RE46567E

(19) United States
(12) Reissued Patent
Kimura

(10) Patent Number: US RE46,567 E
(45) Date of Reissued Patent: Oct. 10, 2017

(54) MAGNETIC RESONANCE IMAGING APPARATUS

(71) Applicant: TOSHIBA MEDICAL SYSTEMS CORPORATION, Otawara-shi, Tochigi (JP)

(72) Inventor: Tokunori Kimura, Yaita (JP)

(73) Assignee: Toshiba Medical Systems Corporation, Otawara-shi, Tochigi-ken (JP)

(21) Appl. No.: 14/986,375

(22) Filed: Dec. 31, 2015

Related U.S. Patent Documents

Reissue of:
(64) Patent No.: 8,624,591
Issued: Jan. 7, 2014
Appl. No.: 13/025,629
Filed: Feb. 11, 2011

(30) Foreign Application Priority Data

Feb. 12, 2010 (JP) ..... 2010-029049
Feb. 7, 2011 (JP) ..... 2011-024332

(51) Int. Cl.
*G01V 3/00* (2006.01)
*A61B 5/055* (2006.01)
(Continued)

(52) U.S. Cl.
CPC ..... *A61B 5/055* (2013.01); *A61B 5/0263* (2013.01); *G01R 33/56333* (2013.01); *G01R 33/5602* (2013.01)

(58) Field of Classification Search
CPC A61B 5/055; A61B 5/0263; G01R 33/56333; G01R 33/5602
(Continued)

(56) References Cited

U.S. PATENT DOCUMENTS 5,846,197 A 12/1998 Edelman
6,023,634 A * 2/2000 Hanawa et al. ..... 600/410
(Continued)

FOREIGN PATENT DOCUMENTS

JP 2009-56072 3/2009

OTHER PUBLICATIONS

Edelman, R.R. MD et al., "Qualitative Mapping of Cerebral Blood Flow and Functional Localization with Echo-Planar MR Imaging and Signal Targeting with Alternating Radio Frequency", Radiology, (1994), vol. 192, pp. 513-520.
(Continued)

*Primary Examiner* — Kenneth J Whittington
(74) *Attorney, Agent, or Firm* — Nixon & Vanderhye, P.C.

(57) ABSTRACT

Provided is an MRI apparatus. In the MRI apparatus, a data collection unit repetitively performs a tag mode of applying an RF wave to at least an upstream portion of an imaging area to perform fluid labeling of a fluid flown into the imaging area and, after a lapse of an inversion time from application of the RF wave, performing magnetic resonance data collection, while changing the inversion time. An image reconstruction unit reconstructs a plurality of tag images corresponding to a plurality of different inversion times based on the magnetic resonance data collected in the tag mode. A reference image generation unit generates a reference image based on the plurality of the tag images. A fluid image generation unit generates a subtraction image
(Continued)

between each of the tag images and the reference image as a fluid image.

31 Claims, 10 Drawing Sheets

(51) Int. Cl.
*G01R 33/563* (2006.01)
*A61B 5/026* (2006.01)
*G01R 33/56* (2006.01)

(58) Field of Classification Search
USPC ..... 324/300–322
See application file for complete search history.

(56) References Cited

U.S. PATENT DOCUMENTS 6,271,665 B1 * 8/2001 Berr ..... G01R 33/56341 324/306
6,564,080 B1 5/2003 Kimura ..... A61B 5/0263 324/307
6,681,132 B1 * 1/2004 Katz et al. ..... 600/410
6,850,793 B1 * 2/2005 Miyazaki et al. ..... 600/410
7,545,141 B2 6/2009 Kimura
7,627,360 B2 12/2009 Kimura
8,125,222 B2 * 2/2012 Sugiura ..... 324/307
8,228,063 B2 * 7/2012 Kimura ..... 324/309
2003/0193334 A1 10/2003 Alsop
2004/0162483 A1 * 8/2004 Kimura ..... G01R 33/56308 600/419
2009/0062640 A1 3/2009 Miyoshi
2009/0309592 A1 * 12/2009 Furudate ..... G01F 1/56 324/306

OTHER PUBLICATIONS

Kwong, K.K. et al., "MR Perfusion Studies with $T_1$-Weighted Echo Planar Imaging", MRM, vol. 34, (1995), pp. 878-887.
Dixon, W.T. et al., "Multiple Inversion Recovery Reduces Static Tissue Signal in Angiograms", Magnetic Resonance in Medicine, vol. 18, (1991), pp. 257-268.
Kitane, S., et al., "Non-Enhanced Time-Resolved MRA Using Inflow Arterial Spin Labeling", Proc. Intl. Soc. Mag. Reson. Med., vol. 17, (2009), p. 3486.
Yan, L. et al., "Quantitative Dynamic MR Angiography Using ASL based TrueFISP", Proc. Intl. Soc. Mag. Reson. Med., vol. 17, (2009), p. 3634.
Mani, S. et al., "Background Suppression with Multiple Inversion Recovery Nulling: Applications to Projective Angiography", MRM, vol. 37, (1997), pp. 898-905.

* cited by examiner

MAGNETIC RESONANCE IMAGING APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is based upon and claims the benefit of priority from Japanese Patent Application No. 2010-029049, filed on Feb. 12, 2010; and Japanese Patent Application No. 2011-024332, filed on Feb. 7, 2011, the entire contents of which are incorporated herein by reference.

FIELD

Embodiments described herein relate to a magnetic resonance imaging (MRI) apparatus.

BACKGROUND

An MRI apparatus is an apparatus which magnetically excites nuclear spins in a subject placed in a static magnetic field, with the use of a Radio Frequency (RF) pulse having Larmor frequency, and then reconstructs an image showing internal structures of the subject based on magnetic resonance signals generated by the excitation. In the related art, there is a method of imaging blood flow by using the MRI apparatus (for example, refer to JP-A 2009-56072 (KOKAI)).

For example, there is an Arterial Spin Labeling (ASL) as an example of a method of imaging blood flow in a non-contrast-enhanced manner (for example, refer to (1) Edelmann R R at al., Radiology 192: 513-519 (1994); (2) KIMURA Tokunori, "non-invasive blood row imaging according to Modified STAR using asymmetric inversion slabs (ASTAR) method" Journal of Japanese Society of Magnetic Resonance in Medicine, 2001, 20 (8), 374-385; (3) Kwong K K, Chester D A, koff R M, Donahue K M, et al., "MR perfusion studies with T1-weighted echo planar imaging", MRM (Mag. Reson. Med), 34: 878-887 (1995); (4) Dixon W T et al., MRM, 18: 257 (1991); and (5) Non-enhanced Time-Resolved MRA using Inflow Arterial Spin Labeling, 2009 ISMRM, pp 3486). In general, in the ASL, the MRI apparatus generates an image of only blood flow components, where stationary tissues are erased, by generating subtraction images between tag images obtained in a tag mode and control images obtained in a control mode.

The tag mode referred herein is, for example, an imaging mode of applying an RF wave to an upstream portion of the artery passing through an imaging area to impart a label referred to as a tag to blood being flown into the imaging area and, and performing imaging after a lapse of an inversion time (TI) after a predetermined label after application of the RF wave. In addition, the control mode is an imaging mode of, after a lapse of a predetermined TI, performing the magnetic resonance data collection without performing the fluid labeling through application of the RF wave to the upstream portion of the imaging area. In other words, the control mode is the imaging mode other than the tag mode among non-contrast-enhanced MRA (MR Angiography) imaging modes. As the control mode, there are, for example, a control mode of performing non-contrast-enhanced imaging, without performing imparting a tag to a fluid, a control mode of imparting a tag to a fluid in an imaging area, a control mode of imparting a tag to a fluid in a downstream portion of the imaging area, or the like.

In addition, there is a method of generating an image of the behavior of a blood flow by repetitively performing ASL with TI being changed. In this method, the MRI apparatus generates an image pair composed of the tag image and the control image for each TI and generates a subtraction image including only a blood flow component for each TI. Hereinafter, a method of collecting an image pair composed of a tag image and a control image for each TI and generating a subtraction image of each image is referred to as an "N–N subtraction method."

In addition, there is a method of generating an image of a blood flow by using only the tag image without generating the subtraction image between the tag image and the control image. For example, there is a method referred as a Multiple IR (mIR) method (for example, refer to Non-enhanced Time-Resolved MRA using Inflow Arterial Spin Labeling, 2009 ISMRM, pp 3487; Quantitative Dynamic MR Angiography using ASL based True FISP., 2009 ISMRM, pp 3635; and Mani S et al., MRM, 37: 898-905 (1997)). In this method, the MRI apparatus applies an area-selective saturation pulse to the imaging area, and after that, an area-non-selective inversion recovery (IR) pulse several times. Next, the MRI apparatus generates a blood flow image, where the signal intensity in the stationary tissue is suppressed, by starting the magnetic resonance data collection at the time where the longitudinal magnetization of the stationary tissue is recovered from a negative value to near zero due to the longitudinal relaxation. Hereinafter, as an mIR method, a method of obtaining a blood flow image without generation of a subtraction image is referred to as an "mIR subtraction-less method."

In addition, a method of simultaneously using the N–N subtraction method and the mIR method is also disclosed (for example, refer to Mani S et al., MRM, 37: 898-905 (1997)). In this method, the MRI apparatus generates a tag image and a control image by using the mIR method and generates a subtraction image between the tag image and the control image. Hereinafter, this method is referred to as an "mIR N–N subtraction method."

The N–N subtraction method is advantageous in that the stationary tissue can be erased with high accuracy but it is problematic in that the imaging time is long. FIG. 15 is a view illustrating a change in signal in association with TI in a known N–N subtraction method. In FIG. 15, the longitudinal axis represents a signal intensity (Stag) of a tag image, and the transverse axis represents TI. As illustrated in FIG. 15, in the N–N subtraction method, the signal intensity (Sstationary illustrated in FIG. 15) in the stationary tissue in the tag image varies according to a change in TI. in addition, similarly to the tag image, the signal intensity in the control image also varies. Therefore, in order to erase the stationary tissue with high accuracy, it is necessary to generate an image pair composed of a tag image and a control image for each TI and to generate a subtraction image for each TI. Accordingly, in the N–N subtraction method, it is necessary to perform two times of data collection (the data collection for the tag image and the data collection for the control image) for the same TI. As a result, the imaging time increases.

In addition, in a conventional mIR subtraction-less method, the imaging time for generating a blood flow image is relatively short because only the tag image used. However, this method is problematic in that it is difficult to adjust the number of applications of the area-non-selective IR pulse and the timing of starting the data collection in order to erase the stationary tissue with high accuracy. In general, the stationary tissue in the imaging area includes plural types of tissues such as fat, cerebrospinal fluid, white matter, and gray matter. However, the longitudinal relaxation time (T1) indicating a time interval from the time of excitation due to the application of an RF wave to the time of recovery to a steady state, is different according to the type of tissue. Therefore, it is difficult to adjust the number of applications of the area-non-selective IR pulse and the timing of starting the data collection so that, for all types of tissues, the time where the longitudinal magnetization is recovered to near zero is coincident with each other. For example, in the case where the number of applications of the area-non-selective IR pulse is set to two, the tissue such as fat, of which the T1 value is short, may remain. in addition, although the number of applications of the area-non-selective IR pulse is set to two and the signal intensity of the tissue, of which the T1 value is short, may be allowed to be near zero, in this case, the signal intensity of the tissue such as cerebrospinal fluid, of which the TI value is long, cannot be allowed to be near zero. In addition, although the signal intensity of the plural types of tissues may be allowed to be near zero by increasing the number of applications of the area-non-selective IR pulse up to three or more, in this case, the imaging time is increased. In this manner, in the mIR subtraction-less method, although the number of applications of the area-non-selective IR pulse and the timing of starting the data collection are adjusted so that the stationary tissue may be erased with high accuracy, there is a limitation in suppressing the background.

In addition, the aforementioned problems occur not only in the case where the blood flow image is imaged but occur also in the case of imaging other fluids (for example, cerebrospinal fluid, or the like).

DETAILED DESCRIPTION

Hereinafter, embodiments of an MRI apparatus will be described in detail with reference to the accompanying drawings. In addition, embodiments of the MRI apparatus are not limited to the below-described ones. For example, the below-described embodiments refer to only the case of imaging a blood flow. However, embodiments may be embodied in cases of imaging various fluids (for example, a cerebrospinal fluid, or the like).

The MRI apparatus according to the embodiment includes a data collection unit, an image reconstruction unit, a reference image generation unit, and a fluid image generation unit. The data collection unit applies an RF wave to an upstream portion of an imaging area or applies the RF wave only to the imaging area, so that a subtraction in strength of a longitudinal magnetization is generated between the upstream portion and the inner portion of the imaging area. The image reconstruction unit reconstructs a plurality of label images corresponding to a plurality of different TIs based on magnetic resonance data collected by the data collection unit. The reference image generation unit generates a reference image based on the plurality of the label images. The fluid image generation unit generates a subtraction image between each of the plurality of the label images and the reference image as a fluid image.

Figure 1:
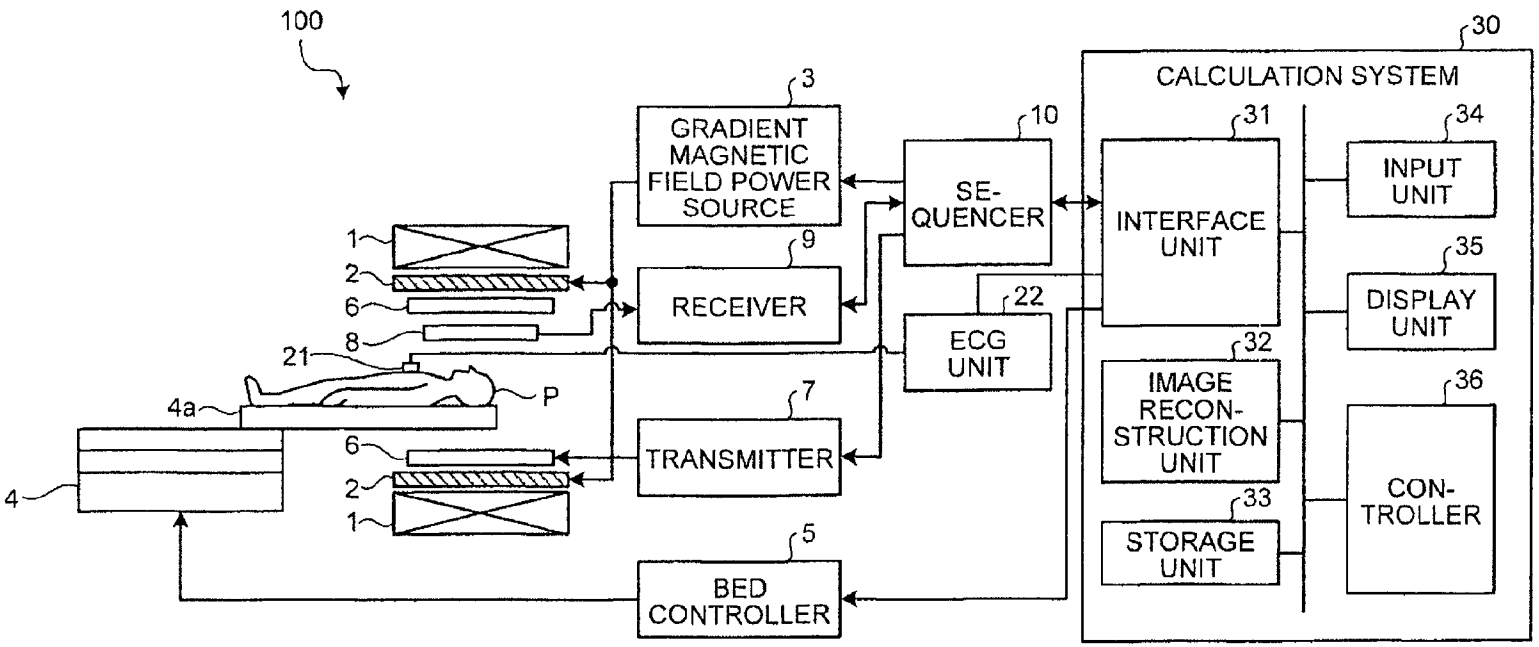
FIG. 1 is a view illustrating the entire configuration of an MRI apparatus according to a first embodiment.

Firstly, an embodiment regarding an mIR subtraction-less method is described as a first embodiment. FIG. 1 is a view illustrating the entire configuration of an MRI apparatus 110 according to the first embodiment. As illustrated in FIG. 1, an MRI apparatus 100 includes a static magnetic field magnet 1, a gradient magnetic field coil 2, a gradient magnetic field power source 3, a bed 4, a bed controller 5, a transmitting RF coil 6, a transmitter 7, a receiving RF coil 8, a receiver 9, a sequencer 10, an Electrocardiogram (ECG) sensor 21, an ECG unit 22, and a calculation system 30.

The static magnetic field magnet 1 is a magnet formed in the shape of a hollow cylinder, which generates a uniform static magnetic field in an inner space. As the static magnetic field magnet 1, for example, a permanent magnet, a superconductor magnet, or the like may be used.

The gradient magnetic field coil 2 is a coil formed in the shape of a hollow cylinder, which is disposed inside the static magnetic field magnet 1. The gradient magnetic field coil 2 is formed as a combination of three coils corresponding to the X, Y, and Z axes perpendicular to one other. The three coils are individually applied with currents from the later-described gradient magnetic field power source 3, so that gradient magnetic fields of which the magnetic field intensities are different in the X, Y, and Z axes can be generated. In addition, the direction of the Z axis is set to be the same as that of the static magnetic field. The gradient magnetic field power source 3 supplies the current to the gradient magnetic field coil 2.

Herein, the gradient magnetic fields in the X, Y, and Z axes generated by the gradient magnetic field coil 2 correspond to, for example, the slice selection gradient magnetic field Gs, the phase encoding gradient magnetic field Ge, and the readout gradient magnetic field Gr. The slice selection gradient magnetic field Gs is used to arbitrarily determine the imaging cross-section. The phase encoding gradient magnetic field Ge is used to change the phase of the magnetic resonance signal according to the spatial position. The readout gradient magnetic field Gr is used to change the frequency of the magnetic resonance signal according to the spatial position.

The bed 4 includes a top board 4a on which the subject P is mounted. Under the control of the later-described bed controller 5, in the state where the subject P is mounted, the top board 4a is inserted into a cavity (imaging entrance) of the gradient magnetic field coil 2. Typically, the bed 4 is disposed in a manner such that the longitudinal direction thereof is parallel to the central axis of the static magnetic field magnet 1. The bed controller 5 is a unit of controlling the bed 4 under the control of a controller 36. The bed controller 5 drives the bed 4 and moves the top board 4a in the longitudinal direction and the upward and downward directions.

The transmitting RF coil 6 is disposed inside the gradient magnetic field coil 2 to be supplied with a high frequency pulse from the transmitter 7 to generate a high frequency magnetic field. The transmitter 7 transmits a high frequency pulse corresponding to Larmor frequency to the transmitting RF coil 6.

The receiving RF coil 8 is disposed inside the gradient magnetic field coil 2 to receive a magnetic resonance signal radiated from the subject P due to the influence of the aforementioned high frequency magnetic field. If the receiving RF coil 8 receives the magnetic resonance signal, the receiving RF coil 8 outputs the magnetic resonance signal to the receiver 9.

The receiver 9 generates the k-space data based on the magnetic resonance signal output from the receiving RF coil 8. More specifically, the receiver 9 generates the k-space data by converting the magnetic resonance signal output from the receiving RF coil 8 into digital signals. The k-space data are mapped to information on the spatial frequencies in a Phase Encode (PE) direction, a Read Out (RO) direction, and a Slice Encode (SE) by the slice selection gradient magnetic field Gs, the phase encoding gradient magnetic field Ge, and the readout gradient magnetic field Gr described above. Next, if the k-space data are generated, the receiver 9 transmits the k-space data to the sequencer 10.

The sequencer 10 scans the subject P by driving the gradient magnetic field power source 3, the transmitter 7, and the receiver 9 based on the sequence information transmitted from the calculation system 30. Herein, the sequence information denotes information defining a procedure for scanning, such as the strength of the power supplied from the gradient magnetic field power source 3 to the gradient magnetic field coil 2, the power supply timing, the strength of the RF signal transmitted from the transmitter 7 to the transmitting RF coil 6, the RF signal transmission timing, and the timing of detection of the magnetic resonance signal in the receiver 9.

In addition, if the subject P is scanned by driving the gradient magnetic field power source 3, the transmitter 7, and as a result, the k-space data are transmitted from the receiver 9, the sequencer 10 transmits the k-space data to the calculation system 30.

The ECG sensor 21 is attached to the surface of the subject P to detect the ECG signals such heartbeat, pulse wave, breath, and the like as electrical signals. The ECG unit 22 applies various processes including an A/D conversion process or a delay process on the ECG signal detected by the ECG sensor 21 to generate a gate signal and transmits the generated gate signal to the sequencer 10.

The calculation system 30 performs control of the entire MRI apparatus 100. For example, the calculation system 30 performs data collection, image reconstruction, or the like by driving the aforementioned components. The calculation system 30 includes an interface unit 31, an image reconstruction unit 32, a storage unit 33, an input unit 34, a display unit 35, and the controller 36.

The interface unit 31 controls transmission and reception of various signals which are exchanged between the calculation system 30 and the sequencer 10. For example, the interface unit 31 transmits the sequence information to the sequencer 10 and receives the k-space data from the sequencer 10. If the k-space data are received, the interface unit 31 stores each of the k-space data for each subject P in the storage unit 33.

The image reconstruction unit 32 applies a post process, that is, a reconstruction process such as Fourier Transform on the k-space data stored in the storage unit 33 to generate image data which visualizes an internal portion of the subject P.

The storage unit 33 stores the k-space data received by the interface unit 31, the image data generated by the image reconstruction unit 32, or the like for each subject P.

The input unit 34 receives various commands or information input from a manipulator. As the input unit 34, a pointing device such as a mouse or a trackball, a selection device such as a mode conversion switch, or an input device such as a keyboard can be appropriately used.

The display unit 35 displays various types of information such as spectrum data or image data under the control of the controller 36. As the display unit 35, a display device such as a liquid crystal display can be used.

The controller 36 includes a Central Processing Unit (CPU) (not shown), a memory, or the like to perform control of the entire MRI apparatus 100. More specifically, the controller 36 controls the scanning by generating the sequence information based on various commands received through the input unit 34 from the manipulator and transmitting the generated sequence information to the sequencer 10 or controls the image reconstruction performed based on the k-space data as a scanning result transmitted from the sequencer 10.

Under the configuration, in the MRI apparatus 100 according to the first embodiment, the sequencer 10 repetitively performs the control mode with TI being changed. In addition, in the first embodiment, the sequencer 10 repetitively performs the control node of applying an RF wave to an imaging area and, after a lapse of a predetermined TI, performing the magnetic resonance data collection instead of performing the blood labeling, through application of the RF wave to an upstream portion of the imaging area, with TI being changed. In other words, in the first embodiment, the sequencer 10 repetitively performs the imaging mode of imparting a tag to blood in the imaging area as the control mode. Next, the calculation system 30 reconstructs a plurality of the control images corresponding to a plurality of different TIs based on the magnetic resonance data collected in the control mode. In addition, the calculation system 30 generates a reference image based on the plurality of the control images and generates a subtraction image between each of the control images and the reference image as a blood flow image.

In other words, the MRI apparatus 100 according to the first embodiment generates the reference image by using the plurality of the control images generated for the TIs and generates the subtraction image between the reference image and each of the control images. In this manner, the method of generating the subtraction image between each of the images generated for each TI and the reference image selected among the images is referred to as an "N−1 subtraction method". According to the N−1 subtraction method, only the control image is used, so that the imaging time is reduced. In addition, by generating the subtraction image, the signal intensity of the stationary tissue other than the blood flow can be suppressed with high accuracy. Therefore, according to the first embodiment, it may be possible to reduce the imaging time and generate the blood flow image where the stationary tissue is erased with high accuracy.

Figure 2:
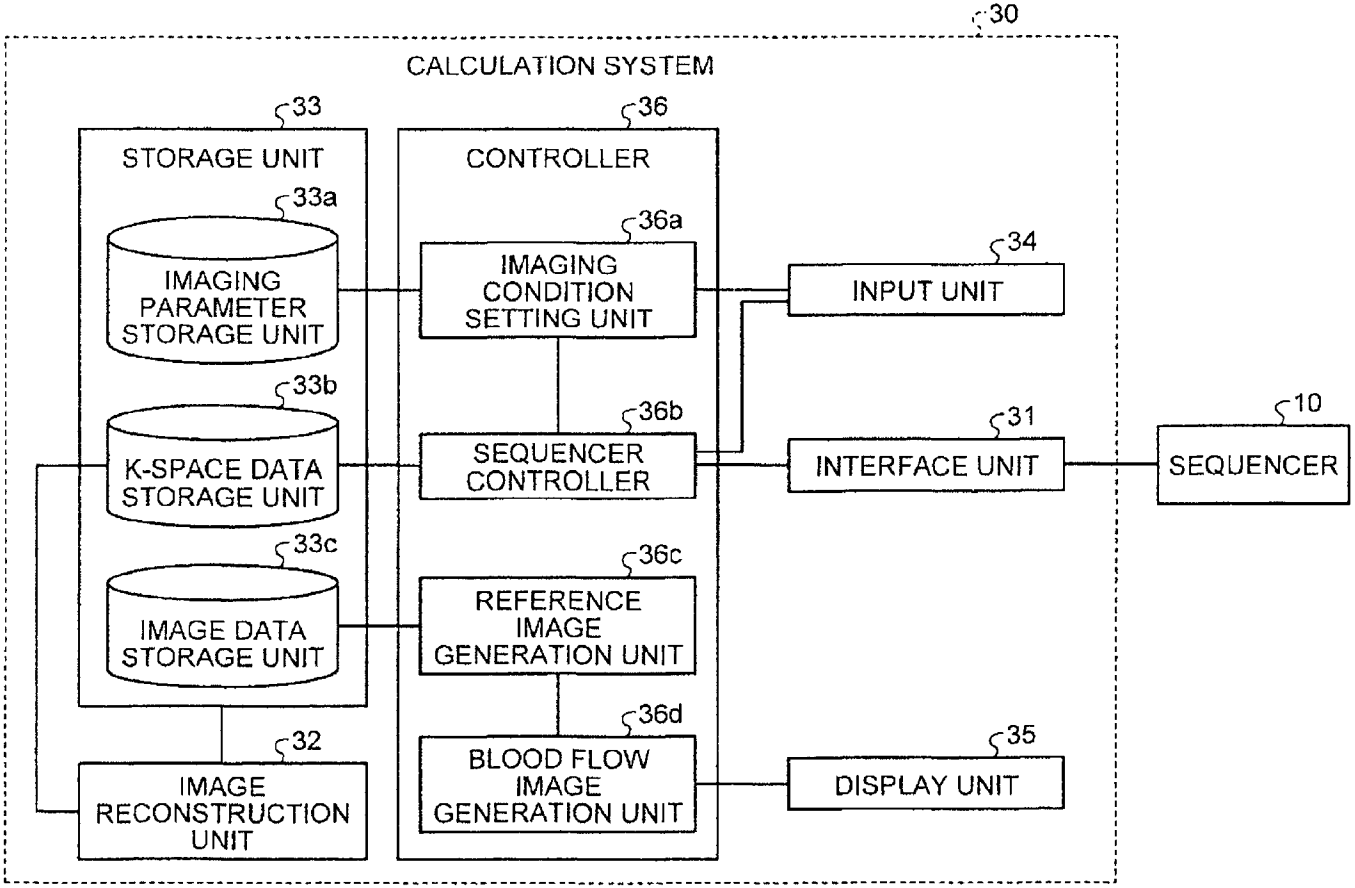
FIG. 2 is a functional block diagram illustrating a detailed configuration of the MRI apparatus according to the first embodiment.

Hereinafter, the MRI apparatus 100 according to the first embodiment is described more in detail. FIG. 2 is a functional block diagram illustrating a detailed configuration of the MRI apparatus 100 according to the first embodiment. FIG. 2 illustrates the sequencer 10 and the calculation system 30 illustrated in FIG. 1. In addition, FIG. 2 illustrates the interface unit 31, the image reconstruction unit 32, the storage unit 33, the input unit 34, the display unit 35, and the controller 36 among the functional units of the calculation system 30.

As illustrated in FIG. 2, the storage unit 33 includes an imaging parameter storage unit 33a, a k-space data storage unit 33b, and an image data storage unit 33c.

The imaging parameter storage unit 33a stores various imaging parameters that are necessary in order to set the imaging condition to obtain the blood flow image. The k-space data storage unit 33b stores the k-space data received through the interface unit 31 from the sequencer 10. The image data storage unit 33c stores the image reconstructed from the k-space data by the image reconstruction unit 32.

In addition, the controller 36 includes an imaging condition setting unit 36a, a sequencer controller 36b, a reference image generation unit 36c, and a blood flaw image generation unit 36d.

The imaging condition setting unit 36a sets the imaging condition based on various commands received through the input unit 34 from the manipulator and the imaging parameters stored in the imaging parameter storage unit 33a.

The sequencer controller 36b generates sequence information based on the imaging condition set by the imaging condition setting unit 36a and transmits the generated sequence information through the interface unit 31 to the sequencer 10. In addition, the sequencer controller 36b stores the k-space data received through the interface unit 31 from the sequencer 10 in the k-space data storage unit 33b.

The reference image generation unit 36c generates a reference image based on a plurality of the control images stored in the image data storage unit 33c. For example, the reference image generation unit 36c selects, among the control images, an image obtained before blood is flown into the imaging area or an image obtained after magnetization of blood in the imaging area is relaxed, and generates the reference image based on the selected image.

The blood flow image generation unit 36d generates a subtraction image between each of the control images reconstructed by the image reconstruction unit 32 and the reference image generated by the reference image generation unit 36c as a blood flow image. In addition, the blood flow image generation unit 36d displays the generated blood flow image.

Figure 3:
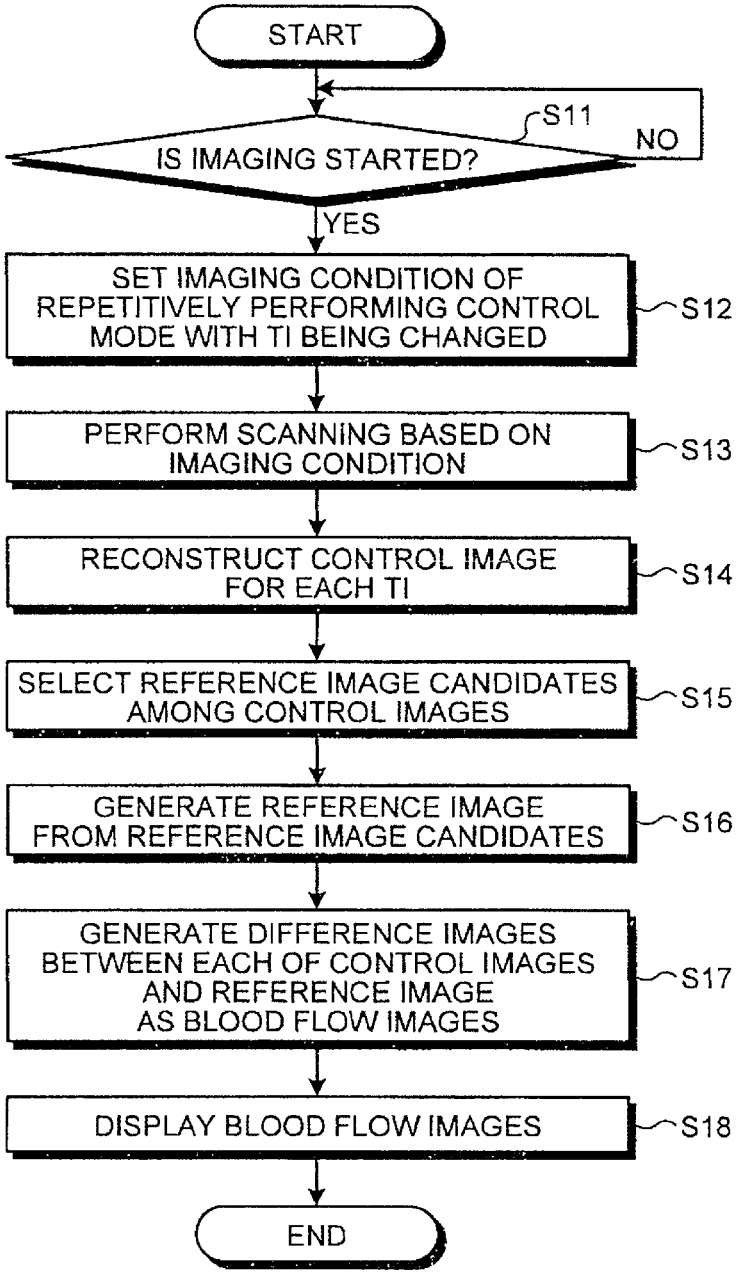
FIG. 3 is a flowchart illustrating a blood flow image generation procedure in a calculation system according to the first embodiment.

Next, a blood flow image generation procedure in the MRI apparatus 100 according to the first embodiment is described. FIG. 3 is a flowchart illustrating the blood flow image generation procedure in the calculation system 30 according to the first embodiment. As illustrated in FIG. 3, in the first embodiment, if the controller 36 receives an imaging start command from the manipulator (Yes in Step S11), the following processes are performed.

First, the imaging condition setting unit 36a sets an imaging condition of repetitively performing the control mode with TI being changed (Step S12). In addition, in the first embodiment, the imaging condition setting unit 36a sets an imaging condition of imparting a tag to blood in the imaging area by applying an area-selective saturation pulse to the imaging area and by performing data collection after a lapse of a predetermined TI from the time of application of the saturation pulse, as an imaging condition of the control mode.

Figure 4:
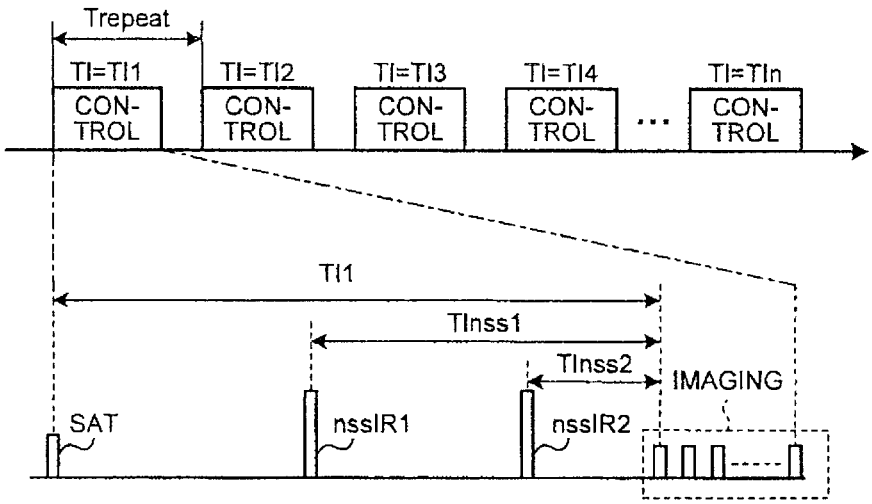
FIG. 4 is a time chart illustrating an example of an imaging condition set by an imaging condition setting unit according to the first embodiment.
Figure 5:
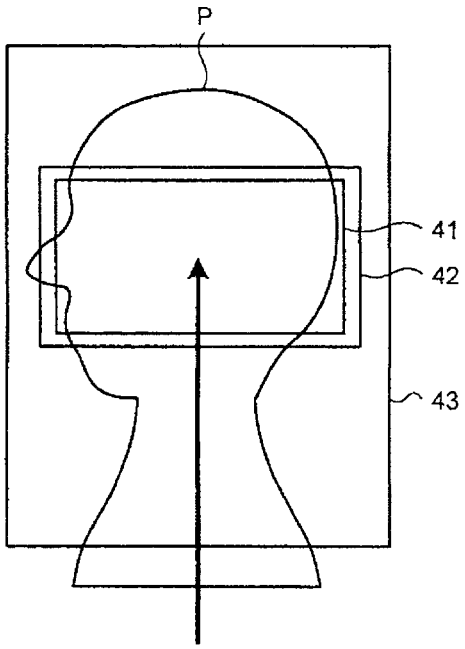
FIG. 5 is a view illustrating an example of an application area and an imaging area for each pulse illustrated in FIG. 4.
Figure 6:
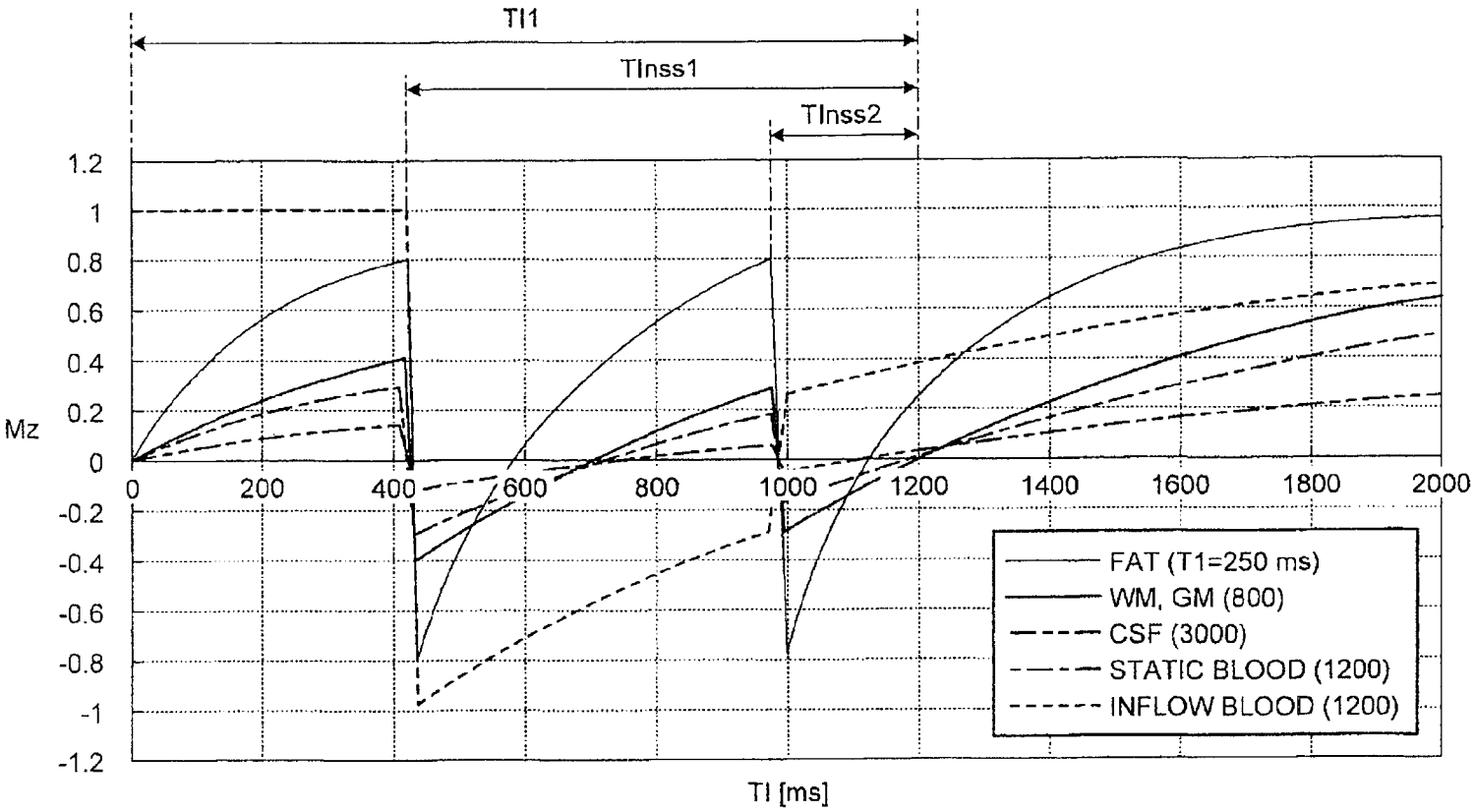
FIG. 6 is a view illustrating a time change of a longitudinal magnetization before and after application of a saturation pulse and an area-non-selective IR pulse illustrated in FIG. 4.

FIG. 4 is a time chart illustrating an example of an imaging condition set by the imaging condition setting unit 36a according to the first embodiment. In addition, FIG. 5 is a view illustrating an example of an application area and an imaging area for each pulse illustrated in FIG. 4. In addition, FIG. 6 is a view illustrating a time change of a longitudinal magnetization before and after the application of a saturation pulse and an area-non-selective IR pulse illustrated in FIG. 4.

As illustrated in FIG. 4, for example, the imaging condition setting unit 36a sets an imaging condition of repetitively performing the control mode (control illustrated in FIG. 4) for each repetition time Trepeat with TI being changed in the order of TI1, TI2, TI3, TI4, . . . TIn. At this time, for example, the imaging condition setting unit 36a sets the TI every 100 ms within a range of from about 100 (shortest) to about 1600 ms.

Next, as illustrated in FIG. 4, in the control mode, first, a saturation pulse SAT having an area selectivity is applied to the imaging area. Herein, the saturation pulse SAT is a 90° pulse. For example, as illustrated in FIG. 5, it is assumed that an imaging area 41 is set to a head portion of the subject P. In addition, the arrow illustrated in FIG. 5 represents a blood flow which is being flown into the imaging area 41. In this case, for example, the saturation pulse SAT is applied to an application area 42 including the imaging area 41. In addition, the application area 42 of the saturation pulse SAT may be coincident with the imaging area 41. In addition, the timing of applying the saturation pulse SAT is controlled based on, for example, a gate signal generated by the ECG unit 22.

If the saturation pulse SAT is applied, the magnetization vector of the tissue included in the application area 42 drops in direction by 90°, so that the longitudinal magnetization becomes zero. FIG. 6 illustrates a change in longitudinal magnetization for fat of T1=250 ms, white matter (WM) and gray matter (GM) of T1=800 ms, cerebrospinal fluid (CSF) of T1=3000 ms, stationary blood of T1=1200 ms influenced by the saturation pulse SAT in the application area 42, and inflow blood of T1=1200 ms being flown into the application area 42. In addition, FIG. 6 illustrates the case where TI1=1200 ms. For example, as illustrated in FIG. 6, if the saturation pulse SAT is applied with TI=0, the longitudinal magnetization of each tissue becomes zero.

After that, as time elapses, the longitudinal magnetization of the tissue included in the imaging area 41 is recovered according to T1 of each tissue. Next, at the time preceding by TInss1 from the starting of the data collection (imaging illustrated in FIG. 4), a first area-non-selective IR pulse nssIR1 is applied. Herein, the area-non-selective IR pulse nssIR1 is a 180° pulse. For example, as illustrated in FIG. 5, the area-non-selective IR pulse nssIR1 is applied to the imaging area 41 and an application area 43 which includes the upstream portion of the blood flowing into the imaging area 41.

Next, if the first area-non-selective IR pulse nssIR1 is applied, the magnetization vector of the tissue in the application area 43 is inverted by 180° to become a negative value. For example, as illustrated in FIG. 6, if the area-non-selective IR pulse nssIR1 is applied at the time preceding by TInss1 from TI1=1200 ms, the longitudinal magnetization of each tissue is inverted to become a negative value.

After that, as time elapses, the longitudinal magnetization of the tissue included in the imaging area 41 is recovered according to T1 of each tissue. Next, at the time preceding by TInss2 from the starting of the data collection (imaging illustrated in FIG. 4), a second area-non-selective IR pulse nssIR2 is applied. Herein, the area-non-selective IR pulse nssIR2 is a 180° pulse. The area-non-selective IR pulse nssIR2 is applied to the application area 43 illustrated in FIG. 5 similarly to the first area-non-selective IR pulse nssIR1.

Next, if the second area-non-selective IR pulse nssIR2 is applied, the magnetization vector of the tissue in the application area 43 is inverted by 180°. Herein, as illustrated in FIG. 6, the TInss2 is set in a manner such that the area-non-selective IR pulse nssIR2 can be applied at the time when the longitudinal magnetization of the blood flown into the application area 42 of the saturation pulse SAT has a negative value and when the longitudinal magnetization of other tissues of which signals must be suppressed has a positive value. Therefore, at the time of applying the area-non-selective IR pulse nssIR2, the longitudinal magnetization of the blood flown into the application area 42 is inverted to a positive value, and the longitudinal magnetization of the tissues of which signals must be suppressed is inverted to a negative value.

In addition, as illustrated in FIG. 6, at the time when the second area-non-selective IR pulse nssIR2 is applied and subsequently when the absolute value of the longitudinal magnetization of the tissues of which signals must be suppressed is within a range that can be considered to be near zero, the data collection from the imaging area 41 is started. For example, FIG. 6 illustrates the case where the timing of starting the data collection is set in a manner such that signal intensities in white matter and gray matter of brain are selectively suppressed. In this manner, if the timing of the starting the data collection is set such that the signal intensity in the stationary tissue can be suppressed, it may be possible to obtain the control image where the signal intensity in the stationary tissue is suppressed.

In addition, the first embodiment relates to the case where the area-non-selective IR pulse is applied twice. However, the area-non-selective IR pulse may be applied once, or three times or more.

In addition, as the imaging sequence for the data collection, for example, Steady State Free Precession (SSFP) is used. Alternatively, Gradient Echo (GRE), Fast Spin Echo (FSE), Echo Planar Imaging (EPI), or the like may be used.

Returning to the description of FIG. 3, if the imaging condition is set by the imaging condition setting unit 36a, the sequencer controller 36b generates the sequence information based on the imaging condition and transmits the sequence information to the sequencer 10. Next, if the sequence information is received, the sequencer 10 performs scanning based on the imaging condition (Step S13). More specifically, the sequencer 10 repetitively performs the control mode of applying the area-selective saturation pulse, which imparts a tag to blood being flown into the imaging area or blood in the imaging area, and of starting, at time of a lapse of a predetermined TI, the magnetic resonance data collection, with the TI being changed.

Subsequently, the image reconstruction unit 32 reconstructs a plurality of the control images corresponding to a plurality of different TIs based on the magnetic resonance data collected in the control mode (Step S14).

After that, the reference image generation unit 36c selects reference image candidates among the plurality of the control images stored in the image data storage unit 33c (Step S15). For example, the reference image generation unit 36c selects the control image obtained before the inflow of the blood to the imaging area among the plurality of the control images reconstructed for each TI. Alternatively, the reference image generation unit 36c selects the control image obtained after the relaxation of magnetization of the blood in the imaging area among the plurality of the control images reconstructed for each TI.

Figure 7:
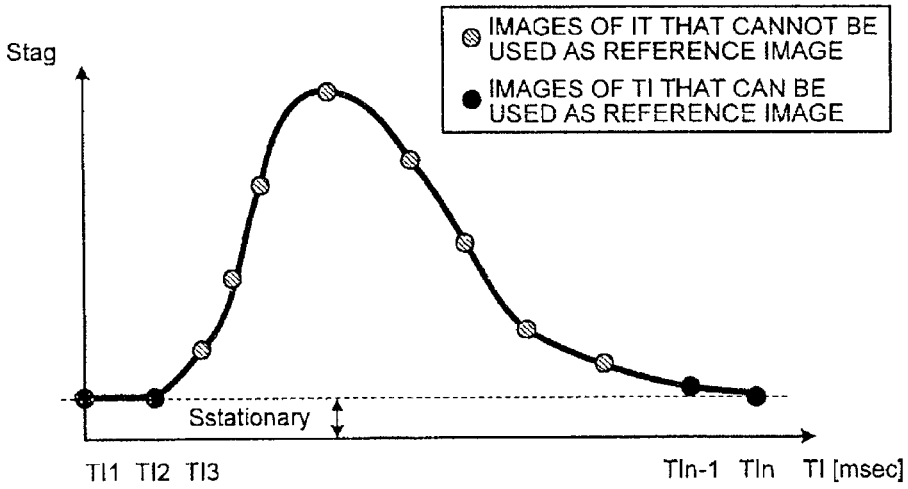
FIG. 7 is a view for explaining a reference image candidate selection performed operation by a reference image generation unit according to the first embodiment.

FIG. 7 is a view for explaining a reference image candidate selection operation performed by the reference image generation unit 36c according to the first embodiment. FIG. 7 illustrates a change in signal value for a plurality of the control images reconstructed for each TI. In FIG. 7, the longitudinal axis represents a signal intensity Stag, and the transverse axis represents TI.

In addition, the signal value referred herein can be obtained, for example, by extracting pixels, of which the pixel value is a threshold value or more, from a plurality of pixels included in a control image and by calculating the average of the extracted pixel values. Alternatively, the signal value referred herein may be the average of the pixel values of pixels included in a Region Of Interest (ROI) set as a vessel portion by a manipulator.

In addition, the threshold value used herein is set in advance to a value by which a signal value representing, for example, air can be erased. Alternatively, for example, a value of 5% maximum pixel value among the pixel values of the pixels included in the control image for the shortest TI may be used as the threshold value. In this case, the same threshold value is used for the control images for all the TIs.

Next, for example, the reference image generation unit 36c selects the control images, each exhibiting a difference in signal intensity, as large as a threshold. value or less, from the signal intensity of the control image obtained when no blood flows, among a plurality of the control images. For example, as illustrated in FIG. 7, the control images corresponding to TI=TI1 to TIn are generated. In this case, the reference image generation unit 36c selects the control images corresponding to TI=TI1, TI2, TIn−1, and TIn as the candidates of the reference image. In other words, the reference image generation unit 36c selects, as the reference image, the control image of which the TI is sufficiently short or the control image of which the TI is sufficiently long. In addition, at this time, one candidate of a plurality of reference image candidates may be selected.

Returning to the description of FIG. 3, the reference image generation unit 36c selects the candidates of the reference image, and after that, generates the reference image from the selected candidates of the reference image (Step S16). For example, the reference image generation unit 36c generates an average image of the plurality of the images selected as the reference image as a reference image. In this manner, by using the average image of the plurality of the images, it may be possible to improve an SN ratio of the reference image. In addition, in the case where the reference image generation unit 36c selects one image as the candidate of the reference image, the reference image generation unit 36c uses the image as the reference image. In other words, the reference image generation operation described herein includes a method of generating a reference image by selecting one image from a plurality of images and a method of directly using one image as the reference image.

In addition, the reference image generation unit 36c may generate a reference image by using a control image exhibiting a small difference in signal intensity between a blood flow portion and a background tissue, among a plurality of control images.

In addition, herein, the case where the reference image generation unit 36c automatically selects the candidates of the reference image is described. However, for example, the reference image generation unit 36c may receive from a manipulator an input as a result of a manipulation of selecting a control image as the candidate of the reference image among a plurality of control images and generate the reference image by using the control image selected by the manipulator. In this case, for example, the reference image generation unit 36c allows a plurality of the control images reconstructed for TIs to be displayed on the display unit 35 and receives from the manipulator an input as a result of a manipulation of selecting one control image or a plurality of control images among the plurality of the displayed control images. Alternatively, for example, as illustrated in FIG. 7, the reference image generation unit 36c displays the information indicating the variation of the signal values of the plurality of the control images reconstructed for each TI on the display unit 35. In this case, as the manipulation of selecting one control image or a plurality of control images, the reference image generation unit 36c receives from the manipulator an input as a result of a manipulation of selecting one information or a plurality of information among information on the plurality of the displayed control images.

After that, the blood flow image generation unit 36d generates the subtraction image between each of the control images reconstructed by the image reconstruction unit 32 and the reference image generated by the reference image generation unit 36c as a blood flow image (Step S17).

Figure 8:
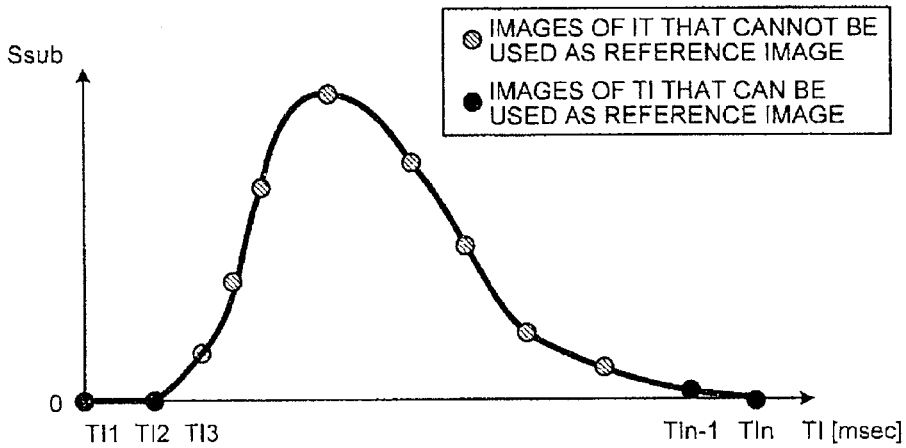
FIG. 8 is a view for explaining a blood flow image generation operation performed by a blood flow image generation unit according to the first embodiment.

FIG. 8 is a view for explaining blood flow image generation performed by the blood flow image generation unit 36d according to the first embodiment. In FIG. 8, the longitudinal axis represents a signal intensity Ssub in the subtraction image, and the longitudinal axis represents TI. In addition, FIG. 8 illustrates the case where an average image of the control images corresponding to TI=TI1, TI2, TIn−1, and TIn illustrated in FIG. 7 is generated as the reference image. In this case, as illustrated in FIG. 8, among the subtraction images generated by the blood flow image generation unit 36d, the signal intensities of the subtraction images corresponding to TI=TI1, TI2, TIn−1, and TIn become near zero. In other words, in the blood flow image generated by the blood flow image generation unit 36d, since the signal intensity in the stationary tissue becomes near zero, the stationary tissue can be erased with high accuracy.

Returning to the description of FIG. 3, the blood flow image generation unit 36d generates the blood flow image, and after that, displays the generated blood flow image on the display unit 35 (Step S18). At this time, for example, the blood flow image generation unit 36d displays a plurality of the generated blood flow image as behavior expression on the display unit 35 in a cine display format or a parallel display format.

As described above, in the first embodiment, the sequencer 10 repetitively performs the control mode of applying an RF wave to the imaging area and, and after a lapse of a predetermined TI, performing magnetic resonance data collection without performing the blood labeling through application of the RF wave to an upstream portion of the imaging area, with the IT being changed. Next, the image reconstruction unit 32 reconstructs a plurality of the control images corresponding to a plurality of different TIs based on the magnetic resonance data collected in the control mode. After that, the reference image generation unit 36c generates a reference image based on the plurality of the control images. In addition, the blood flow image generation unit 36d generates a subtraction image between each of the control images and the reference image as a blood flow image. Therefore, according to the first embodiment, it is possible to reduce the imaging time and to generate the blood flow image where the stationary tissue is erased with high accuracy.

In addition, in the first embodiment, at the time of performing the control mode, the sequencer 10 applies a non-selective inversion recovery pulse to a range including the imaging area and the blood flown into the imaging area so that the magnetic resonance data collection is started at the time when the longitudinal magnetization of at least one type of tissue among the tissues included in the imaging area becomes substantially zero. Therefore, according to the first embodiment, since the control image, of which the signal intensity in the stationary tissue is suppressed, can be reconstructed, so that it may be possible to generate the blood flow image where the stationary tissue is erased with higher accuracy.

In addition, in the first embodiment, the reference image generation unit 36c selects among the control images an image obtained before blood is flown into the imaging area or an image obtained after magnetization of blood in the imaging area is relaxed, and generates the reference image based on the selected image. Therefore, according to the first embodiment, it may be possible to generate the blood flow image without a decrease in signal intensity in the blood flow portion.

In addition, in the first embodiment, the reference image generation unit 36c selects a plurality of the images obtained before blood is flown into the imaging area or a plurality of the images obtained after magnetization of blood in the imaging area is relaxed, and generates an average image of the plurality of the selected images as the reference image. Therefore, according to the first embodiment, since the SN ratio of the reference image can improve, it may be possible to obtain the blood flow image with higher accuracy.

In addition, in the first embodiment, the sequencer 10 uses the SSFP as the imaging sequence for the magnetic resonance data collection. In general, in the SSFP, in order to allow the longitudinal magnetization to be in the steady state, a plurality of dummy pulses needs to be applied at the starting of the data collection. Therefore, in the SSFP, the TI or Trepeat is increased, so that the imaging time also increases. However, according to the first embodiment, since the number of dummy pulses can be decreased in comparison with a conventional mIR subtraction-less method, it may be possible to obtain the shortest TI or Trepeat.

In addition, in a modified example of the aforementioned first embodiment, for example, the sequencer 10 may be configured in a manner such that, before the magnetic resonance data collection is started, a saturation pulse is applied to a range including the imaging area. FIG, 9 is a time chart illustrating an example of an imaging condition set by the imaging condition setting unit 36a according to a modification of the first embodiment. In addition, FIG. 10 is a view illustrating an example of an application area and an imaging area for each pulse illustrated in FIG. 9.

Figure 9:
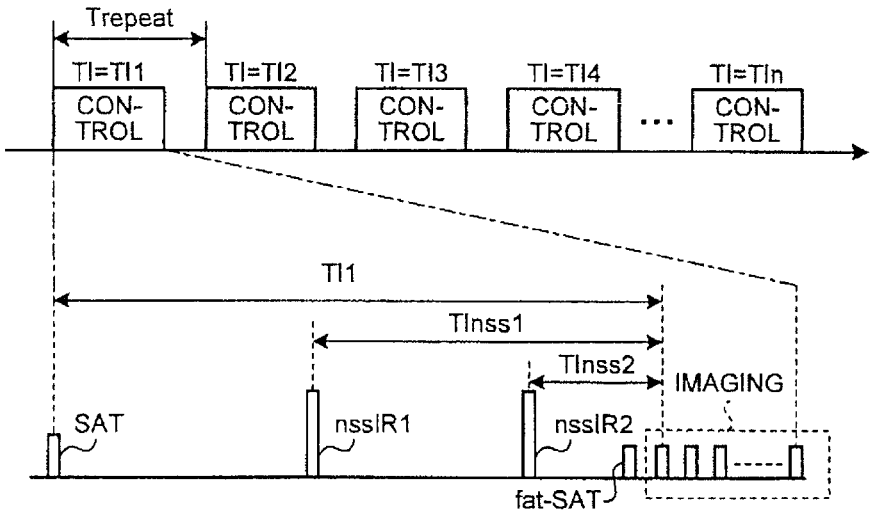
FIG. 9 is a time chart illustrating an example of an imaging condition set by the imaging condition setting unit according to a modification of the first embodiment.
Figure 10:
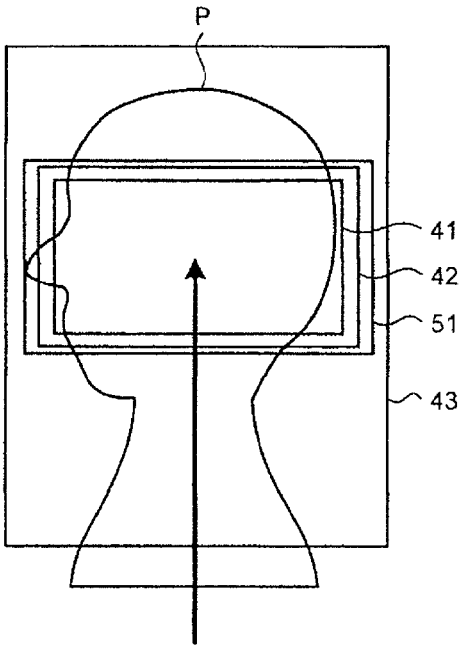
FIG. 10 is a view illustrating an example of an application area and an imaging area for each pulse illustrated in FIG. 9.

As illustrated in FIG. 9, for example, the imaging condition setting unit 36a applies a saturation pulse fat-SAT for suppressing a signal intensity of fat just before the data collection (imaging, illustrated in FIG. 9) is started. For example, as illustrated in FIG. 10, the saturation pulse fat-SAT is applied to an application area 51 including the imaging area 41. Therefore, even in the case where the TI is allowed to be changed, the signal intensity of the tissues such as fat, of which the TI value is short, is almost constant. Furthermore, by allowing the blood flow image generation unit 36d to generate a subtraction image, it may be possible to erase the signal intensity of the tissue such as fat, of which the TI value is short, with high accuracy.

Next, an mIR N–N subtraction method according to the second embodiment is described. In addition, the configuration of the MRI apparatus according to the second embodiment is the same as those illustrated in FIGS. 1 and 2.

In the second embodiment, the sequencer 10 repetitively performs the tag mode of performing fluid labeling of a fluid flown into the imaging area by applying an RF wave to at least an upstream portion of the imaging area and, after a lapse of TI from application of the RF wave, performing the magnetic resonance data collection, with the TI being changed. Next, the calculation system 30 reconstructs a plurality of the tag images corresponding to a plurality of different TIs based on the magnetic resonance data collected in the tag mode. In addition, the calculation system 30 generates a reference image based on the plurality of the tag images and generates subtraction images each between the reference image and each of the tag images In addition, in the second embodiment, the sequencer 10 performs the control mode of applying an RF wave to an imaging area and, after a lapse of TI, performing the magnetic resonance data collection without performing of the blood flow labeling through application of the RF wave to an upstream portion of the imaging area by performance number smaller than that of the tag mode. In addition, the calculation system 30 further reconstructs the control images, of which the number is smaller than that of the tag images, based on the magnetic resonance data collected in the control mode.

Next, the calculation system 30 generates one reference image by using the control images, of which the number is smaller than that of the tag images, and generates subtraction images between the generated reference image and the plurality of the tag images. In this manner, the method of generating one reference image from control images, of which the number is smaller than that of tag images, and generating subtraction images between the tag images and the reference image is referred to as an "N–M collection N–1 subtraction method." In addition, N and M are natural numbers, and $1 \leq M < N$.

Alternatively, the calculation system 30 generates a plurality of control images for subtraction corresponding to a plurality of different TIs by using the control images of which the number is smaller than that of the tag images. Next, the calculation system 30 generates subtraction images between the tag images and the generated control images for the TIs. In this manner, a method of generating the control images for subtraction, of which the number is equal to that of the tag images, from the control images, of which the number is smaller that that of the tag images, and generating the subtraction images between the tag images and the generated control images for the TIs is referred to as an "N–M collection N–N subtraction method."

Figure 11:
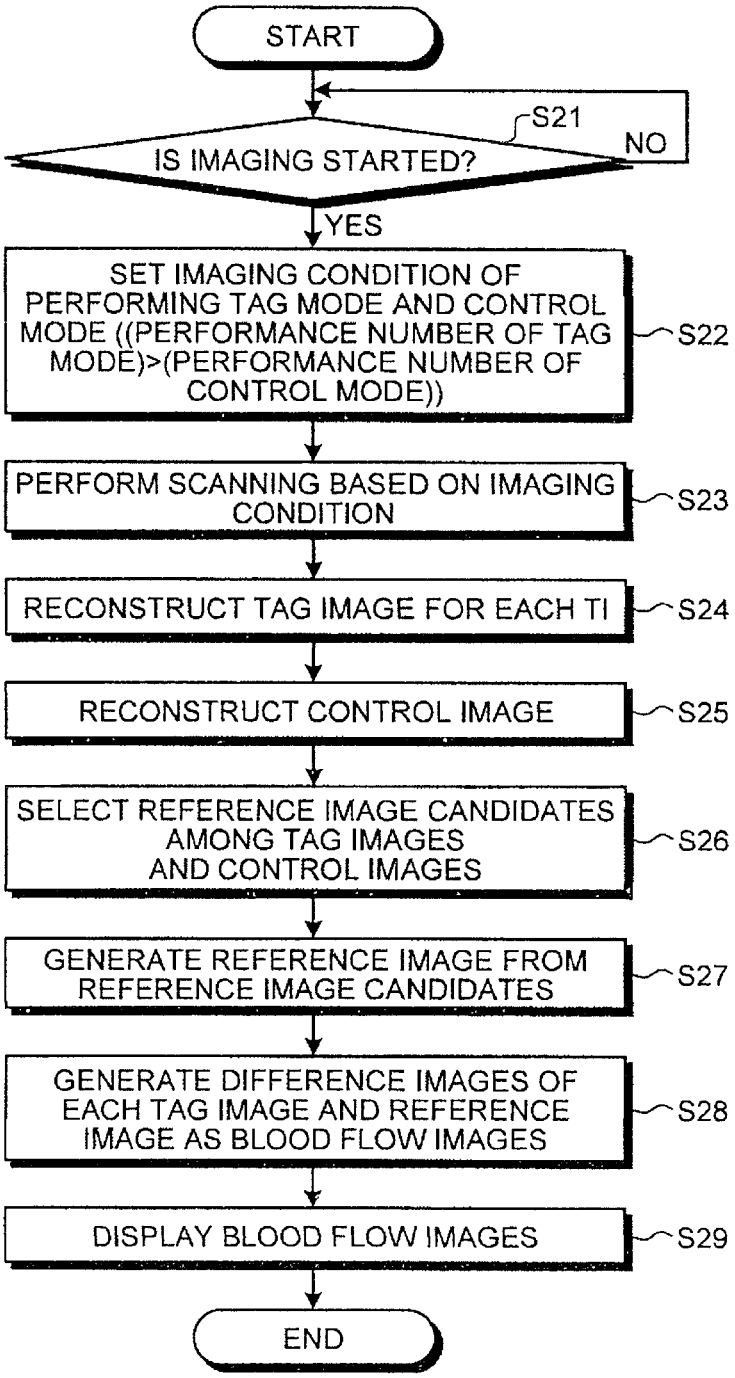
FIG. 11 is a flowchart illustrating a blood flow image generation procedure in a calculation system according to a second embodiment.

Hereinafter, a blood flow image generation procedure in the MRI apparatus according to the second embodiment is described. FIG. 11 is a flowchart illustrating the blood flow image generation procedure in the calculation system 30 according to the second embodiment. As illustrated in FIG. 11, in the second embodiment, if the controller 30 receives an imaging start command from a manipulator (Yes in Step S21), the following processes are performed.

First, the imaging condition setting unit 36a sets an imaging condition of individually performing the tag mode and the control mode. In addition, in the second embodiment, the imaging condition setting unit 36a sets an imaging condition of imparting a tag to blood in an area including an imaging area and an upstream portion of the imaging area by applying an IR pulse to the area and, after a lapse of a predetermined TI from application of the IR pulse, performing imaging, as an imaging condition of the tag mode. In addition, in the second embodiment, the imaging condition setting unit 36a sets an imaging condition of imparting a tag to blood in the imaging area by applying an IR pulse to the imaging area and, after a lapse of a predetermined TI from application of a saturation pulse, performing data collection, as an imaging condition of the control mode.

In addition, at this time, the imaging condition setting unit 36a sets the imaging condition so that the tag mode can be repetitively performed with the TI being changed and the control mode is performed a given number of times that is smaller than the number of performances of the tag mode (Step S22).

Figure 12:
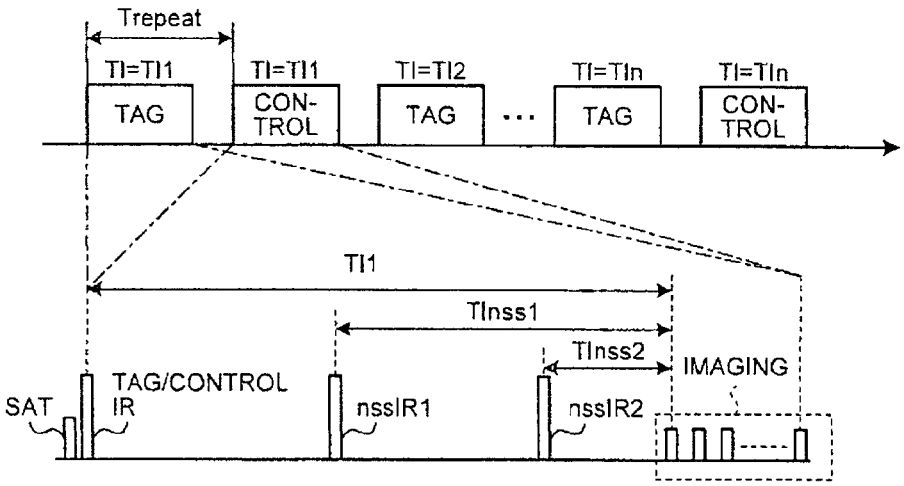
FIG. 12 is a time chart illustrating an example of an imaging condition set by an imaging condition setting unit according to the second embodiment.
Figure 13:
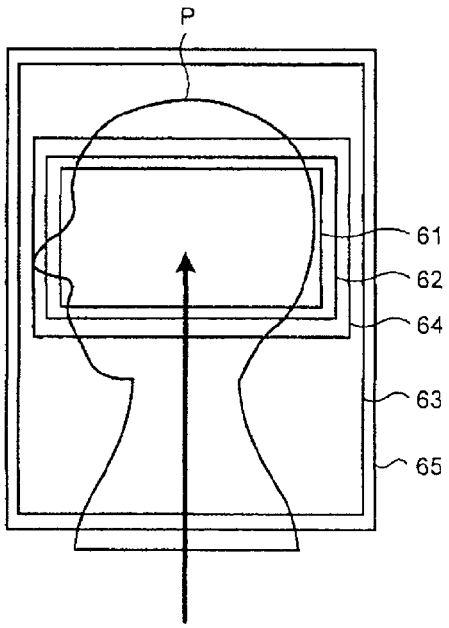
FIG. 13 is a view illustrating an example of an application area and an imaging area for each pulse illustrated in FIG. 12.

FIG. 12 is a time chart illustrating an example of the imaging condition set by an imaging condition setting unit 36a according to the second embodiment. In addition, FIG. 13 is a view illustrating an example of the application area and the imaging area for each pulse illustrated in FIG, 12.

As illustrated in FIG. 12, for example, the imaging condition setting unit 36a sets an imaging condition of repetitively performing the tag mode (tag illustrated in FIG. 12) for each repetition time Trepeat while changing the TI in the order of TI1, TI2, TI3, TI4, . . . TIn. At this time, the imaging condition setting unit 36a sets an imaging condition for the control mode in a manner such that the control mode is performed for only some portion of the TIs TI1 to TIn. In other words, the imaging condition setting unit 36a sets the imaging condition in a manner such that the performance number of the control mode is smaller than that of the tag mode.

In this manner, since the imaging condition setting unit 36a sets the imaging condition in a manner such that the control mode is performed by the performance number smaller than that of the tag mode, it may be possible to reduce the imaging time in comparison with conventional N–N subtraction method or the mIR N–N subtraction method where the tag mode and the control mode are performed for each TI.

Next, as illustrated in FIG. 12, in the tag mode, first, a saturation pulse SAT having an area selectivity is applied to the imaging area. Herein, the saturation pulse SAT is a 90° pulse, For example, as illustrated in PIG. 13, it is assumed that an imaging area 61 is set to a head portion of the subject P. In addition, the arrow illustrated in FIG. 13 represents a blood flow which is being flown into the imaging area 61. In this case, for example, the saturation pulse SAT is applied to an application area 64 including the imaging area 61. In addition, the application area 64 of the saturation pulse SAT may be coincident with the imaging area 61. In addition, the timing of applying the saturation pulse SAT is controlled based on, for example, a gate signal generated by the ECG unit 22. In addition, the influence of application of the saturation pulse SAT on tissues is the same as that described in first embodiment, description thereof will not be repeated herein.

After application of the saturation pulse SAT, an IR pulse tag IR for the tag mode is applied. Herein, the IR pulse tag IR is a 180° pulse. For example, as illustrated in FIG. 13, the IR pulse tag IR is applied to an application area 63 including the imaging area 61 and an upstream portion of the imaging area 61. Therefore, the magnetization vector in the tissue located in the application area 63 is inverted by 180°.

After that, at time preceding by TInss1 from the starting of the data collection (imaging illustrated in FIG. 12), the first area-non-selective IR pulse nssIR1 is applied. In addition, after the area-non-selective IR pulse nssIR1 is applied, at the time preceding by TInss2 from the starting of the data collection (imaging illustrated in FIG. 12), the second area-non-selective IR pulse nssIR2 is applied. Herein, each of the area-non-selective IR pulses nssIR1 and nssIR2 is a 180° pulse. For example, as illustrated in FIG. 13, the area-non-selective IR pulses nssIR1 and nssIR2 are applied to an application area 65 including the imaging area 61 and an upstream portion of the imaging area 61. In addition, the influence of application of the area-non-selective IR pulses nssIR1 and nssIR2 on tissues is the same as that described in first embodiment, description thereof will not be repeated herein.

Next, similarly to the first embodiment, after the second area-non-selective IR pulse nssIR2 is applied, at the time when the absolute value of the longitudinal magnetization of the tissues where signals are suppressed becomes within a range which the absolute value is considered to be near zero, the data collection from the imaging area 61 is started.

On the other hand, in the control mode, as illustrated in FIG. 12, first, an area-selective saturation pulse SAT is applied to the imaging area. Herein, the saturation pulse SAT is a 90° pulse. In an example illustrated in FIG. 13, similarly to the tag mode, for example, the saturation pulse SAT is applied to the application area 64.

After application of the saturation pulse SAT, an IR pulse control IR for the control mode is applied. Herein, the IR pulse control IR is a 180° pulse. For example, as illustrated in FIG. 13, the IR pulse control IR is applied to an application area 62 including the imaging area 61. Therefore, the magnetization vector in the tissue located in the application area 62 is inverted by 180°.

After that, at the time preceding by TInss1 from the starting of the data collection (imaging illustrated in FIG. 12), the first area-non-selective IR pulse nssIR1 is applied. In addition, after the area-non-selective IR pulse nssIR1 is applied, at the time preceding by TInss2 from the starting of the data collection (imaging illustrated in FIG. 12), the second area-non-selective IR pulse nssIR2 is applied. For example, as illustrated in FIG, 13, similarly to the tag mode, the area-non-selective IR pulses nssIR1 and nssIR2 are applied to the application area 65. In addition, the influence of application of the area-non-selective IR pulses nssIR1 and nssIR2 on tissues is the same as that described in first embodiment, description thereof will not be repeated herein.

Next, similarly to the first embodiment, after the second area-non-selective IR pulse nssIR2 is applied, at the time when the absolute value of the longitudinal magnetization of the tissues where signals are suppressed becomes within a range which the absolute value is considered to be near zero, the data collection from the imaging area 61 is started.

In addition, similarly to the first embodiment, as the imaging sequence for the data collection in the tag mode and the control mode, for example, SSFP (Steady State Free Precession) is used. Alternatively, GRE (Gradient Echo), FSE (Fast Spin Echo), EPI (Echo Planar Imaging), or the like may be used.

In addition, it is preferable that the imaging condition setting unit 36a sets the imaging condition so that the control mode is performed with the same collection condition as the collection condition used at the time of performing the tag mode. Therefore, even in the case where a fat suppressing pulse is not applied just before the data collection is started, the signal intensity in the stationary tissue can be maintained uniform between the tag mode and the control mode, so that it is possible to erase the stationary tissue with higher accuracy.

In addition, FIG. 12 illustrates an example where the tag mode and the control mode are performed for the same TI. However, for example, the imaging condition setting unit 36a may set the imaging condition so that, after the tag mode is performed for all the TIs, the control mode is performed by performance number smaller than that of the tag mode. Alternatively, on the contrary, the imaging condition setting unit 36a may set the imaging condition so that, after the control mode is performed, the tag mode is performed.

Returning to the description of FIG. 11, if the imaging condition is set by the imaging condition setting unit 36a, the sequencer controller 36b generates the sequence information based on the imaging condition and transmits the sequence information to the sequencer 10. Next, if the sequence information is received, the sequencer 10 performs scanning based on the imaging condition (Step S23). More specifically, the sequencer 10 repetitively performs the tag mode with the TI being changed and performs the control mode by performance number smaller than that of the tag mode.

Subsequently, the image reconstruction unit 32 reconstructs a plurality of the tag images corresponding to a plurality of different TIs based on the magnetic resonance data collected in the tag mode (Step S24). In addition, the image reconstruction unit 32 reconstructs at least one control image based on the magnetic resonance data collected in the control mode (Step S25).

After that, similarly to the first embodiment, the reference image generation unit 36c selects the candidates of the reference image among the plurality of the tag images and the control images stored in the image data storage unit 33c (Step S26). For example, the reference image generation unit 36c selects among the plurality of the tag images and the control images an image before blood is flown into the imaging area. Alternatively, the reference image generation unit 36c selects among the plurality of the tag images reconstructed for the TIs an image after magnetization of blood in the imaging area is relaxed. In addition, at this time, one candidate of the reference image of a plurality of candidates of the reference image may be selected.

Returning to the description of FIG. 11, after the reference image generation unit 36c selects the candidates of the reference image, the reference image generation unit 36c generates a reference image from the selected candidates of the reference image (Step S27). For example, the reference image generation unit 36c generates an average image of a plurality of the images, which are selected as the candidates of the reference image, as the reference image. In this manner, by using the average image of the plurality of the images, it is possible to improve the SN ratio of the reference image. In addition, when the reference image generation unit 36c selects one image as the candidate of the reference image, the reference image generation unit 36c uses the image as the reference image. In other words, the reference image generation referred herein includes generation of the reference image from a plurality of the images and usage of one image as the reference image.

In addition, the reference image generation unit 36c may generate a reference image by using images, of which the difference in signal between a blood flow portion and a background tissue is small, among a plurality of the tag images and the control images.

After that, the blood flow image generation unit 36d generates a subtraction image between each of the tag images reconstructed by the image reconstruction unit 32 and the reference image generated by the reference image generation unit 36c as a blood flow image (Step S28). Herein, similarly to the first embodiment, in the blood flow image generated by the blood flow image generation unit 36d, since the signal intensity in the stationary tissue becomes near zero, the stationary tissue can be erased with high accuracy.

Returning to the description of FIG. 11, the blood flow image generation unit 36d generates the blood flow image, and after that, displays the generated blood flow image on the display unit 35 (Step S29). At this time, for example, the blood flow image generation unit 36d displays a plurality of the generated blood flow image as behavior display on the display unit 35 in a cine display format or a parallel display format.

As described above, in the second embodiment, the sequencer 10 repetitively performs the tag mode of performing blood labeling of the blood being flown into the imaging area by applying an IR pulse to an upstream portion of the imaging area and after a lapse of a predetermined TI from application of the IF pulse, performing the magnetic resonance data collection, with the TI being changed. In addition, the sequencer 10 performs the control mode of applying an RF wave to the imaging area and, after a lapse of a predetermined TI, performing the magnetic resonance data without performing the blood labeling through application of the IR pulse to the upstream portion of the imaging area by performance number smaller than that of the tag mode. Next, the image reconstruction unit 32 reconstructs a plurality of the tag images corresponding to a plurality of different TIs based on the magnetic resonance data collected in the tag mode. In addition, the image reconstruction unit 32 reconstructs at least one control image based on the magnetic resonance data collected in the control mode. After that, the reference image generation unit 36c generates a reference image based on the plurality of the tag images and the control image. In addition, the blood flow image generation unit 36d generates a subtraction image between each of the tag images and the reference image as a fluid image. Therefore, according to the second embodiment, it is possible to reduce the imaging time and to generate the blood flow image where the stationary tissue is erased with high accuracy.

In addition, in the second embodiment, the sequencer 10 performs the control mode with the same collection condition as the collection condition used at the time of performing the tag mode. Therefore, even in the case where a fat suppressing pulse is not applied just before the data collection is started, the signal intensity in the stationary tissue can be maintained uniform between the tag mode and the control mode, so that it is possible to erase the stationary tissue with higher accuracy.

In addition, in the second embodiment, the case where Flow-sensitive Alternating Inversion Recovery (FAIR) series method of imparting a tag to blood in the imaging area is performed by the sequencer 10 is described. However, for example, the case where the Signal Targeting with Alternating Radio frequency (STAR) series method of imparting a tag to blood flown into the imaging area is performed by the sequencer 10 is also implemented.

In addition, in the second embodiment, the subtraction images between one reference image and a plurality of the tag images are generated as the blood flow images. However, for example, the reference images of which the number is equal to that of the tag images may be generated by interpolating the control images. In this case, the reference image generation unit 36c generates a plurality of the reference images corresponding to a plurality of different TIs based on the control images. Next, the blood flow image generation unit 36d generates subtraction images between the tag image and the reference images as the blood flow images for the TIs.

For example, the reference image generation unit 36c generates control images for subtraction, of which the number is equal to that of the tag images, from the control images for the TIs, of which the number is smaller than that of the collected tag images, by performing a calculation process such model function fitting. In the case where at least two control images exist, the reference image generation unit 36c may generate a plurality of the control images for subtraction through linear approximation. In addition, in the case where three control images exist, the reference image generation unit 36c may generate a plurality of the control images for subtraction through quadratic function approximation.

In this manner, even in the case where the signal intensity in the stationary tissue is changed according to the TI, by generating the control images for subtraction, of which the number is equal to that of the tag images, and generating the subtraction images for the TIs, it is possible to generate the blood flow image where the stationary tissue is erased with high accuracy.

In addition, in the second embodiment, at the time of performing the tag mode and the control mode, similarly to the first embodiment, the sequencer 10 applies non-selective inversion recovery pulse to a range including the imaging area and the blood flown into the imaging area so that the magnetic resonance data collection is started at the time when the longitudinal magnetization of at least one type of tissue among the tissues included in the imaging area becomes substantially zero. Therefore, according to the second embodiment, since the tag image where the signal intensity in the stationary tissue is suppressed can be reconstructed, so that it is possible to generate the blood flow image where the stationary tissue is erased with higher accuracy.

In addition, in the second embodiment, similarly to the first embodiment, the reference image generation unit 36c selects among the tag images an image before blood is flown into the imaging area or an image after magnetization of blood in the imaging area is relaxed and generates the reference image based on the selected image. Therefore, according to the second embodiment, it is possible to generate the blood flow image without a decrease in signal intensity in the blood flow portion.

In addition, in the second embodiment, similarly to the first embodiment, the reference image generation unit 36c selects a plurality of the images before blood is flown into the imaging area or a plurality of the images after magnetization of blood in the imaging area is relaxed and generates an average image of the plurality of the selected images as the reference image. Therefore, according to the second embodiment, since the SN ratio of the reference image can be improved, it is possible to obtain the blood flow image with higher accuracy.

In addition, similarly to the first embodiment, in the second embodiment, the sequencer 10 uses the SSFP as the imaging sequence of the time of collecting the magnetic resonance data. In general, in the SSFP, in order to allow the longitudinal magnetization to be in the steady state, a plurality of the dummy pulses need to be applied at the starting of the data collection, so that the TI or Trepeat is increased. In addition, as a result, the imaging time is also increased. However, according to the second embodiment, since the number of dummy pulses can be reduced in comparison with a conventional mIR N−N subtraction method, it is possible to obtain the shortest TI or Trepeat.

In addition, in the second embodiment, similarly to the first embodiment, the sequencer 10 may apply the saturation pulse to the range including the imaging area before the starting of the magnetic resonance data collection. Therefore, in the case where the TI is allowed to be changed, since the signal intensity of the tissue such as fat, of which the T1 value is short, is almost the same, so that it is possible to erase the signal intensity of the tissue such as fat, of which the T1 value is short, with high accuracy.

In addition, in the first and second embodiment, the case of using a single tag & single TI method where the sequencer 10 applies the IR pulse for the tag allocation at every time when the data collection is performed is described. However, the embodiment may be implemented in the case of using, for example, a single tag & multi TI method where the sequencer 10 applies the IR pulse once and, after that, continuously perform the data collection multiple times.

Figure 14:
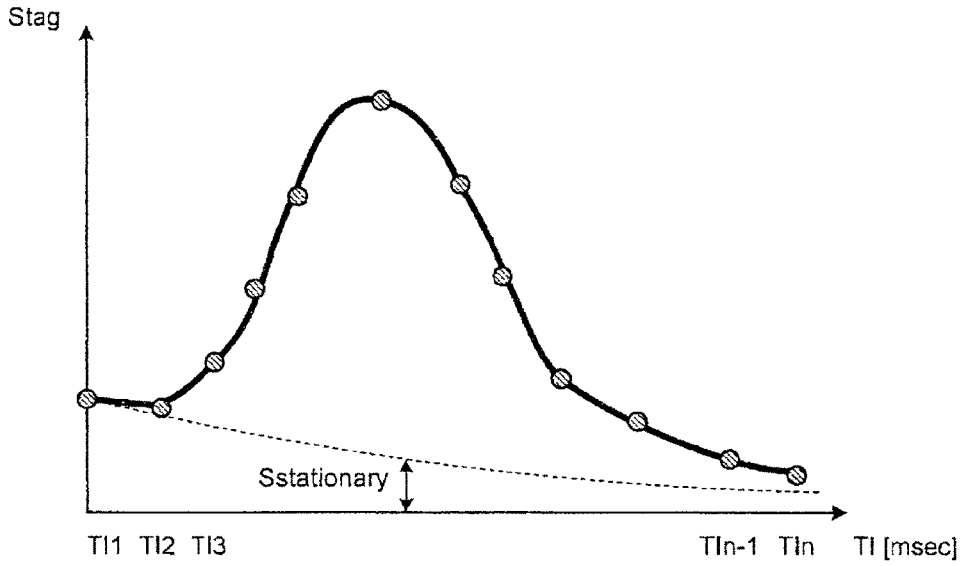
FIG. 14 is a view illustrating attenuation of a signal intensity in a single tag & multi TI method according to a modification of the embodiment.
Figure 15:
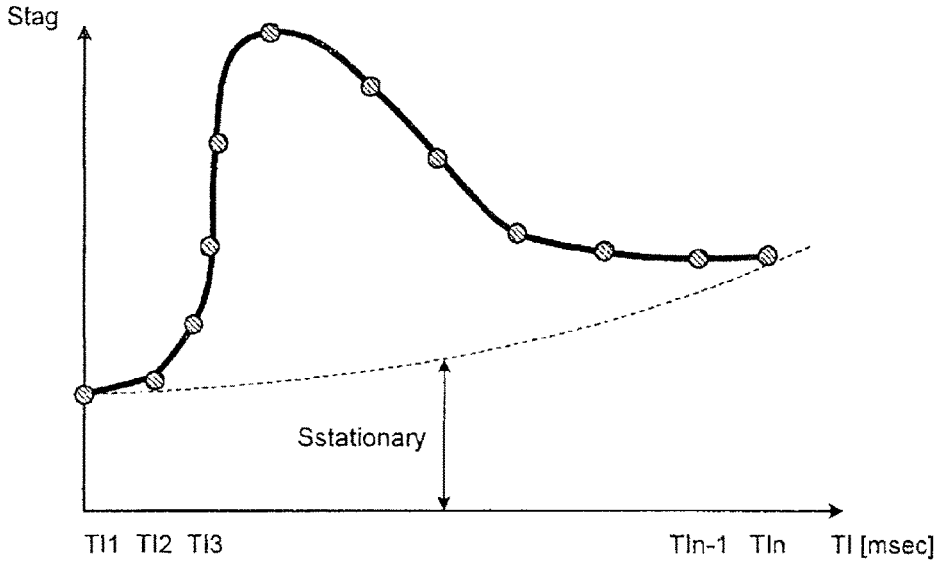
FIG. 15 is a view illustrating a change in signal with respect to TI in a conventional N–N subtraction method.

In addition, in the single tag & multi TI method, in general, since the longitudinal magnetization is insufficiently recovered, the TI becomes long, so that the signal intensity of each tissue is attenuated. FIG. 14 is a view illustrating attenuation of a signal intensity in the single tag & multi TI method according to a modified example of the embodiment. In this case, as illustrated in FIG. 14, in the tag image, as the TI is increased, the signal intensity (Sstationary illustrated in FIG. 14) in the stationary tissue is attenuated. Therefore, for example, longitudinal relaxation correction may be performed on the generated blood flow image.

In this case, the blood flow image generation unit 36d performs the relaxation correction on the blood flow image according to the TI based on the T1 value of the blood. For example, when the T1 value of the blood is denoted by T1 blood, the blood flow image generation unit 36d performs correction of scaling an inverse function 1/exp[−TI/T1blood] for correcting the longitudinal relaxation of the blood. Alternatively, for example, the blood flow image generation unit 36d performs correction using a function having an after-labeling TI, the number of IR pulses m in the mIR method, a T1 value T1blood of the blood, a repetition time TR of an excited pulse in the data collection, the number of encodes N for each shot in the data collection, and a repetition time Trepeat of IR pulse for tag allocation as variables. In addition, if the blood flow signal is obtained after the differentiation, in the case where quantification of Cerebral Blood Flow (CBF) is not a purpose but imaging of vessel behavior is a purpose, the correction of the signal intensity for each of the TIs is not necessarily performed.

In addition, in the first and second embodiments, the case where the area-non-selective IR pulse or the saturation pulse is applied to the imaging area is described. However, for example, the sequencer 10 may be configured so that the sequencer 10 applies the RF wave for performing blood flow labeling to the upstream portion of the downstream portion of the imaging area and applies no RF wave to the imaging area until the TI elapses after application of the RF wave.

In addition, in the first and second embodiments, the case where an inversion recovery pulse for performing the blood flow labeling is applied for a short time is described. However, recently, as a method of performing the blood flow labeling of the blood flow flown into the imaging area, there has been disclosed a method of continuously or intermittently applying an inversion recovery pulse. In the other embodiments, this method may be used. In this case, for example, the MRI apparatus continuously or intermittently applies an inversion recovery pulse for performing the labeling to an upstream side of a imaging area, and performs the magnetic resonance data collection while fixing or changing the TI that indicates an waiting time from the time of application of the inversion pulse to the time of imaging of the imaging area (the time of application of a high frequency excitation pulse). In addition, the MRI apparatus reconstructs a plurality of MR images corresponding to a plurality of different TIs based on the collected magnetic resonance data. Next, the MRI apparatus generates a reference image based on a plurality of the reconstructed MR images and generates subtraction images between each of the MR images and the reference image as the blood flow images. Alternatively, the MRI apparatus may use as the reference image, among the reconstructed MR images, an MR image (tag image) in which a fluid applied a continuous or pulsed continuous inversion pulse at a tagging area on an upstream side of an imaging area has not reached at the imaging area. In addition, MR images each subtracted with the reference image are not limited to a plurality of MR images each corresponding to a plurality of TIs, but may be one or more images. In addition, the inversion recovery pulse for performing the labeling is not limited to the RF pulse, but a continuous RF wave may be used. Herein the RF pulse and the continuous RF wave are collectively referred as an RF wave.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:

*a memory; and*

*a processor comprising processing circuitry, wherein the memory stores instructions, which when executed by the processor, cause the magnetic resonance imaging apparatus to perform operations comprising:*

[a data collection unit that] repetitively [performs] *performing* a tag mode of applying an RF wave to at least an upstream portion of an imaging area to label a fluid flown into the imaging area and, after a lapse of an inversion time from application of the RF wave, performing magnetic resonance data collection, while changing the inversion time;

[an image reconstruction unit that reconstructs] *reconstructing* a plurality of tag images corresponding to a plurality of different inversion times based on magnetic resonance data collected in the tag mode;

[a reference image generation unit that generates] *generating* a reference image based on the plurality of [the] tag images; and

[a fluid image generation unit that generates] *generating* a subtraction image between each of the tag images and the reference image as a fluid image.

2. The magnetic resonance imaging apparatus according to claim 1, wherein the [reference image generation unit generates] *instructions, when executed by the processor, cause the magnetic resonance imaging apparatus to generate* the reference image by using the tag image exhibiting a small difference in signal intensity between a blood flow portion and a background tissue among the plurality of [the] tag images.

3. The magnetic resonance imaging apparatus according to claim 1, [further comprising] *wherein the instructions, when executed by the processor, cause the magnetic resonance imaging apparatus to*:

[a display unit that displays] *display* a plurality of the fluid images generated by the fluid image generation unit as behavior expression in a cine display format or a parallel display format.

4. The magnetic resonance imaging apparatus according to claim 1, wherein at the time of performing the tag mode, [the data collection unit applies] *the instructions, when executed by the processor, cause the magnetic resonance imaging apparatus to apply* a non-selective inversion recovery pulse to a range including the imaging area and the fluid flown into the imaging area so that the magnetic resonance data collection is started at the time when a longitudinal magnetization of at least one type of tissue among tissues included in the imaging area becomes nearly zero.

5. The magnetic resonance imaging apparatus according to claim 1, wherein the [data collection unit applies] *instructions, when executed by the processor, cause the magnetic resonance imaging apparatus to apply* a saturation pulse to a range including the imaging area just before the magnetic resonance data collection is started.

6. The magnetic resonance imaging apparatus according to claim 1, wherein the [reference image generation unit selects] *instructions, when executed by the processor, cause the magnetic resonance imaging apparatus to select* among the tag images an image obtained before the fluid is flown into the imaging area or an image obtained after magnetization of the fluid in the imaging area is relaxed, and [generates] *to generate* the reference image based on the selected image.

7. The magnetic resonance imaging apparatus according to claim 6, wherein the [reference image generation unit selects] *instructions, when executed by the processor, cause the magnetic resonance imaging apparatus to select* a plurality of images obtained before the fluid is flown into the imaging area or a plurality of images obtained after magnetization of the fluid in the imaging area is relaxed, and [generates] *to generate* an average image of the plurality of the selected images as the reference image.

8. The magnetic resonance imaging apparatus according to claim 1, wherein the [data collection unit further performs] *instructions, when executed by the processor, cause the magnetic resonance imaging apparatus to perform* a control mode a given number of times that is smaller than the number of performances of the tag mode, the control mode being an imaging mode of applying an RF wave to the imaging area without labeling a fluid through application of an RF wave to an upstream portion of the imaging area and, after a lapse of an inversion time from application of the RF wave, [performing] *to perform* magnetic resonance data collection, wherein the [image reconstruction unit further reconstructs] *instructions, when executed by the processor, cause the magnetic resonance imaging apparatus to reconstruct* control images as many as a number smaller than that of the tag images, based on the magnetic resonance data collected in the control mode, wherein the [reference image generation unit generates] *instructions, when executed by the processor, cause the magnetic resonance imaging apparatus to generate* one reference image or a plurality of control images for subtraction corresponding to the plurality of different inversion times by using the control images as many as a number smaller than that of the tag images, and wherein the [fluid image generation unit generates] *instructions, when executed by the processor, cause the magnetic resonance imaging apparatus to generate* a subtraction image between each of the tag images and the reference image or [generates] *to generate* a subtraction image between the tag image and the generated control image for each inversion time.

9. The magnetic resonance imaging apparatus according to claim 8, wherein the [data collection unit performs] *instructions, when executed by the processor, cause the magnetic resonance imaging apparatus to perform* the control mode under a collection condition which is the same as the collection condition used at the time of performing the tag mode.

10. The magnetic resonance imaging apparatus according to claim 1, wherein the [data collection unit uses] *instructions, when executed by the processor, cause the magnetic resonance imaging apparatus to use* Steady State Free Precession (SSFP), Gradient Echo (GRE), Fast Spin Echo (FSE), or Echo Planar Imaging (EPI) as an imaging sequence for magnetic resonance data collection.

11. The magnetic resonance imaging apparatus according to claim 1, wherein the [fluid image generation unit further performs] *instructions, when executed by the processor, cause the magnetic resonance imaging apparatus to perform* longitudinal relaxation correction on the fluid image according to the inversion time based on a T1 value of the fluid.

12. The magnetic resonance imaging apparatus according to claim 1, wherein the [data collection unit applies] *instructions, when executed by the processor, cause the magnetic resonance imaging apparatus to apply* the RF wave for performing the fluid labeling to the upstream portion or downstream portion of the imaging area and [applies] *to apply* no RF wave to the imaging area until a predetermined inversion time elapses from application of the RF wave.

13. A magnetic resonance imaging apparatus comprising:

*a memory; and*

*a processor comprising processing circuitry, wherein the memory stores instructions, which when executed by the processor, cause the magnetic resonance imaging apparatus to perform operations comprising:*

[a data collection unit that repetitively performs] *repetitively performing* a control mode of applying an RF wave to an imaging area without labeling a fluid through application of an RF wave to an upstream portion of the imaging area and, after a lapse of an inversion time from application of the RF wave, performing magnetic resonance data collection[,]while changing the inversion time;

[an image reconstruction unit that reconstructs a plurality of control images corresponding to a plurality of different inversion times based on the magnetic resonance data collected in the control mode;

a reference image generation unit that generates] *generating* a reference image based on the plurality of [the]control images; and

[a fluid image generation unit that generates] *generating* subtraction images between each of the control images and the reference image as fluid images.

14. The magnetic resonance imaging apparatus according to claim 13, wherein the [reference image generation unit generates] *instructions, when executed by the processor, cause the magnetic resonance imaging apparatus to generate* the reference image by using the control image exhibiting a small difference in signal intensity between a blood flow portion and a background tissue among the plurality of [the]control images.

15. The magnetic resonance imaging apparatus according to claim 13, [further comprising: a display unit that displays] *wherein the instructions, when executed by the processor, cause the magnetic resonance imaging apparatus to display* a plurality of the fluid images generated by the fluid image generation unit as behavior expression in a cine display format or a parallel display format.

16. The magnetic resonance imaging apparatus according to claim 13, wherein *the instructions, when executed by the processor, cause the magnetic resonance imaging apparatus to,* at the time of performing the control mode, [the data collection unit applies] *apply* a non-selective inversion recovery pulse to a range including the imaging area and the fluid flown into the imaging area so that the magnetic resonance data collection is started at the time when a longitudinal magnetization of at least one type of tissue among tissues included in the imaging area becomes nearly zero.

17. The magnetic resonance imaging apparatus according to claim 13, wherein the [data collection unit applies] *instructions, when executed by the processor, cause the magnetic resonance imaging apparatus to apply* a saturation pulse to a range including the imaging area just before the magnetic resonance data collection is started.

18. The magnetic resonance imaging apparatus according to claim 13, wherein the [reference image generation unit selects] *instructions, when executed by the processor, cause the magnetic resonance imaging apparatus to select* among the control images an image obtained before the fluid is flown into the imaging area or an image obtained after magnetization of the fluid in the imaging area is relaxed, and [generates] *to generate* the reference image based on the selected image.

19. The magnetic resonance imaging apparatus according to claim 18, wherein the [reference image generation unit selects] *instructions, when executed by the processor, cause the magnetic resonance imaging apparatus to select* a plurality of images obtained before the fluid is flown into the imaging area or a plurality of images obtained after magnetization of the fluid in the imaging area is relaxed, and [generates] *to generate* an average image of the plurality of the selected images as the reference image.

20. A magnetic resonance imaging apparatus comprising:

*a memory; and*

*a processor comprising processing circuitry, wherein the memory stores instructions, which when executed by the processor, cause the magnetic resonance imaging apparatus to perform operations comprising:*

[a data collection unit that repetitively performs] *repetitively performing* an imaging mode of applying an RF wave to a subject to label a fluid flown into the subject and, after a lapse of an inversion time from application of the RF wave, performing magnetic resonance data collection while changing the inversion time;

[an image reconstruction unit that reconstructs] *reconstructing* a plurality of images corresponding to a plurality of different inversion times based on the magnetic resonance data;

[a reference image generation unit that generates] *generating* a reference image based on the plurality of the images; and

[a fluid image generation unit that generates] *generating* a subtraction image between each of the images and the reference image as a fluid image.

21. A magnetic resonance imaging apparatus comprising:

*a memory; and*

*a processor comprising processing circuitry, wherein the memory stores instructions, which when executed by the processor, cause the magnetic resonance imaging apparatus to perform operations comprising:*

[a data collection unit that repetitively performs] *repetitively performing* an imaging mode of applying an RF wave to a subject to label a fluid flown into the subject and, after a lapse of an inversion time from application of the RF wave, performing magnetic resonance data collection of an imaging area while changing the inversion time;

[an image reconstruction unit that reconstructs] *reconstructing* a plurality of images corresponding to a plurality of different inversion times based on the magnetic resonance data; *and*

[a fluid image generation unit that generates] *generating* a fluid image by generating a subtraction image between at least one of the plurality of the images and a reference image, the reference image being an image obtained before the labeled fluid is flown into the imaging area or an image obtained after magnetization of a fluid in the imaging area is relaxed.

*22. A magnetic resonance imaging apparatus comprising:*

*a memory; and*

*a processor comprising processing circuitry, wherein the memory stores instructions, which when executed by the processor, cause the magnetic resonance imaging apparatus to perform operations comprising:*

*repetitively performing a tag mode to collect magnetic resonance data while changing an inversion time, and perform a control mode to collect magnetic resonance data a given number of times that is smaller than the number of performances of the tag mode;*

*reconstructing a plurality of tag images corresponding to a plurality of different inversion times based on the magnetic resonance data collected in the tag mode, and reconstructing one or more control images as many as a number smaller than that of the tag images based on the magnetic resonance data collected in the control mode; and*

*generating a subtraction image for each inversion time using the tag images and the one or more control images.*

*23. The magnetic resonance imaging apparatus according to claim 22, wherein,*

*the tag mode applies a first RF wave to an area that includes an upstream portion of an imaging area to label a fluid flown into the imaging area and, after a lapse of the inversion time from application of the first RF wave, performs the magnetic resonance data collection, and*

*the control mode applies a second RF wave to an area that does not include the upstream portion and, after a lapse of the inversion time from application of the second RF wave, performs the magnetic resonance data collection.*

*24. The magnetic resonance imaging apparatus according to claim 22, wherein*

*the instructions, when executed by the processor, cause the magnetic resonance imaging apparatus to generate a first image using the one or more control images, and*

*to generate the subtraction image for each inversion time by generating a subtraction image between each of the plurality of tag images and the first image.*

*25. The magnetic resonance imaging apparatus according to claim 22, wherein*

*the instructions, when executed by the processor, cause the magnetic resonance imaging apparatus to generate a plurality of second images corresponding to the plurality of different inversion times using the one or more control images, and*

*to generate the subtraction image for each inversion time by generating a subtraction image between the tag image and the second image for each inversion time.*

*26. A magnetic resonance imaging apparatus comprising:*

*a memory; and*

*a processor comprising processing circuitry, wherein the memory stores instructions, which when executed by the processor, cause the magnetic resonance imaging apparatus to perform operations comprising:*

*performing a tag mode, and performing a control mode a given number of times that is smaller than the number of performances of the tag mode, the tag mode applying a first RF wave to at least an upstream portion of an imaging area to label a fluid flown into the imaging area and, after a lapse of an inversion time from application of the first RF wave, performing collection of magnetic resonance data, while changing the inversion time, the control mode performing collection of magnetic resonance data without labeling a fluid through application of an RF wave to the upstream portion of the imaging area;*

*reconstructing a plurality of tag images corresponding to a plurality of different inversion times based on the magnetic resonance data collected in the tag mode, and reconstructing one or more control images as many as a number smaller than that of the tag images based on the magnetic resonance data collected in the control mode; and*

*generating a subtraction image for each inversion time using the tag images and the one or more control images.*

*27. The magnetic resonance imaging apparatus according to claim 26, wherein:*

*the tag mode applies the first RF wave to an area that includes the upstream portion, and*

*the control mode applies a second RF wave to an area that does not include the upstream portion and, after a lapse of the inversion time from application of the second RF wave, performs collection of the magnetic resonance data.*

*28. The magnetic resonance imaging apparatus according to claim 26, wherein*

*the instructions, when executed by the processor, cause the magnetic resonance imaging apparatus to generate a first image using the one or more control images, and*

*to generate the subtraction image for each inversion time by generating a subtraction image between each of the plurality of tag images and the first image.*

*29. The magnetic resonance imaging apparatus according to claim 26, wherein*

*the instructions, when executed by the processor, cause the magnetic resonance imaging apparatus to generate a plurality of second images corresponding to the plurality of different inversion times using the one or more control images, and*

*to generate the subtraction image for each inversion time by generating a subtraction image between the tag image and the second image for each inversion time.*

*30. A magnetic resonance imaging method comprising:*

*repetitively performing a tag mode to collect magnetic resonance data while changing an inversion time;*

*performing a control mode to collect magnetic resonance data a given number of times that is smaller than the number of performances of the tag mode;*

*reconstructing a plurality of tag images corresponding to a plurality of different inversion times based on the magnetic resonance data collected in the tag mode;*

*reconstructing one or more control images as many as a number smaller than that of the tag images based on the magnetic resonance data collected in the control mode; and*

*generating a subtraction image for each inversion time using the tag images and the one or more control images.*

*31. A magnetic resonance imaging method comprising:*

*repetitively performing a tag mode, the tag mode applying an RF wave to at least an upstream portion of an imaging area to label a fluid flown into the imaging area and, after a lapse of an inversion time from application of the RF wave, performing collection of magnetic resonance data, while changing the inversion time;*

*performing a control mode a given number of times that is smaller than the number of performances of the tag mode, the control mode performing collection of magnetic resonance data without labeling a fluid through application of an RF wave to the upstream portion of the imaging area;*

*reconstructing a plurality of tag images corresponding to a plurality of different inversion times based on the magnetic resonance data collected in the tag mode;*

*reconstructing one or more control images as many as a number smaller than that of the tag images based on the magnetic resonance data collected in the control mode; and*

*generating a subtraction image for each inversion time using the tag images and the one or more control images.*

* * * * *